US009132262B2

(12) United States Patent
Berman et al.

(10) Patent No.: US 9,132,262 B2
(45) Date of Patent: Sep. 15, 2015

(54) APPLICATOR FOR DISPENSING A MEDICINAL SUBSTANCE

(76) Inventors: Irwin R. Berman, Saint Simons Island, GA (US); Richard D. Gillespie, III, Athens, TX (US); Gervasio Salgado, Marbella (ES); Armand Maaskamp, Napa, CA (US); Ryan Maaskamp, San Francisco, CA (US)

( * ) Notice: Subject to any disclaimer, the term of this patent is extended or adjusted under 35 U.S.C. 154(b) by 0 days.

(21) Appl. No.: 13/573,394

(22) Filed: Sep. 13, 2012

(65) Prior Publication Data

US 2013/0085456 A1 Apr. 4, 2013

Related U.S. Application Data

(60) Continuation-in-part of application No. 13/064,467, filed on Mar. 28, 2011, now Pat. No. 8,845,596, which is a continuation of application No. 11/541,985, filed on Oct. 2, 2006, now abandoned, which is a division of application No. 10/446,739, filed on May 29, 2003, now Pat. No. 7,125,394, which is a continuation-in-part of application No. 10/160,166, filed on Jun. 4, 2002, now Pat. No. 7,141,036.

(51) Int. Cl.
*A61M 31/00* (2006.01)
*B65B 1/00* (2006.01)
*A61M 5/32* (2006.01)
*A61M 5/315* (2006.01)

(52) U.S. Cl.
CPC .......... *A61M 31/007* (2013.01); *A61M 5/3291* (2013.01); *A61M 31/00* (2013.01); *B65B 1/00* (2013.01); *A61M 5/31505* (2013.01); *A61M 5/329* (2013.01); *Y10T 29/49826* (2015.01)

(58) Field of Classification Search
CPC ... A61M 31/007; A61M 5/007; A61M 5/329; A61M 5/3291
USPC .............. 604/15, 57–60, 275, 279, 310, 311
See application file for complete search history.

(56) References Cited

U.S. PATENT DOCUMENTS

| | | | | | |
|---|---|---|---|---|---|
| 3,109,427 | A | * | 11/1963 | Davidson | 604/212 |
| 3,667,461 | A | * | 6/1972 | Zamarra | 604/212 |
| 4,311,140 | A | * | 1/1982 | Bridgman | 604/22 |
| 4,906,239 | A | * | 3/1990 | Bruhl et al. | 604/275 |
| 5,451,216 | A | * | 9/1995 | Quinn | 604/270 |
| 5,695,481 | A | * | 12/1997 | Heinzelman et al. | 604/279 |
| 5,843,043 | A | * | 12/1998 | Markus | 604/239 |
| 7,090,654 | B2 | * | 8/2006 | Lotito et al. | 604/43 |
| 7,125,394 | B2 | * | 10/2006 | Berman et al. | 604/60 |
| 7,322,953 | B2 | * | 1/2008 | Redinger | 604/43 |
| 7,465,295 | B2 | * | 12/2008 | Bergeron et al. | 604/279 |
| 8,092,415 | B2 | * | 1/2012 | Moehle et al. | 604/6.16 |

(Continued)

*Primary Examiner* — Andrew Gilbert
(74) *Attorney, Agent, or Firm* — J. Bruce Hoofnagle

(57) ABSTRACT

An applicator 270 includes a stem 174 having an axially-formed slot delivery passage 200. A slot 176 is formed transaxially through the stem 174 and is in communication with the slot delivery passage 200. An extended side wall 176b is formed on one side of the slot 176. A flat surface 276 is formed in the stem 174 and extends angularly away from an opposite side of the slot 176 and from the extended side wall 176b to provide a wide slot opening at an external surface 195 of the stem for dispensing a cream from the opening. A trough-like cleft 306 can be formed in the external surface 195 of a solid portion of the stem 174, distally of the slot 176, to provide an axially-extended path for the cream being dispensed through the slot.

28 Claims, 21 Drawing Sheets

(56) References Cited

U.S. PATENT DOCUMENTS

| | | |
|---|---|---|
| 2004/0193102 A1* | 9/2004 | Haggstrom ..................... 604/43 |
| 2005/0033222 A1* | 2/2005 | Haggstrom et al. ............ 604/43 |
| 2008/0300575 A1* | 12/2008 | Cleator et al. ................. 604/514 |
| 2009/0112153 A1* | 4/2009 | Gregersen et al. .............. 604/43 |
| 2009/0118661 A1* | 5/2009 | Moehle et al. ............... 604/6.16 |

* cited by examiner

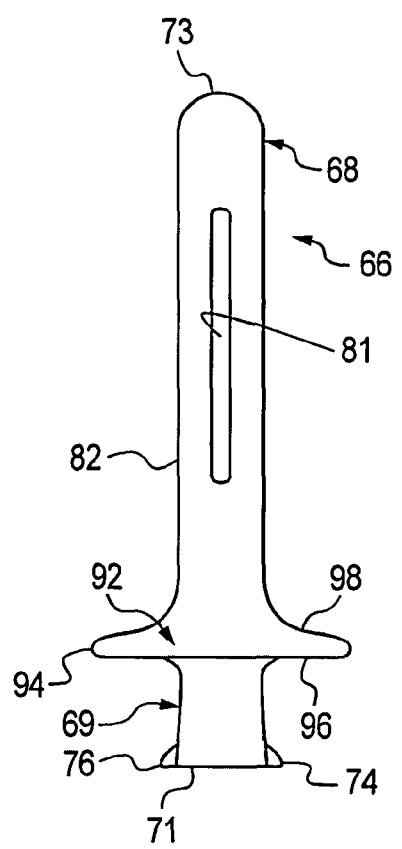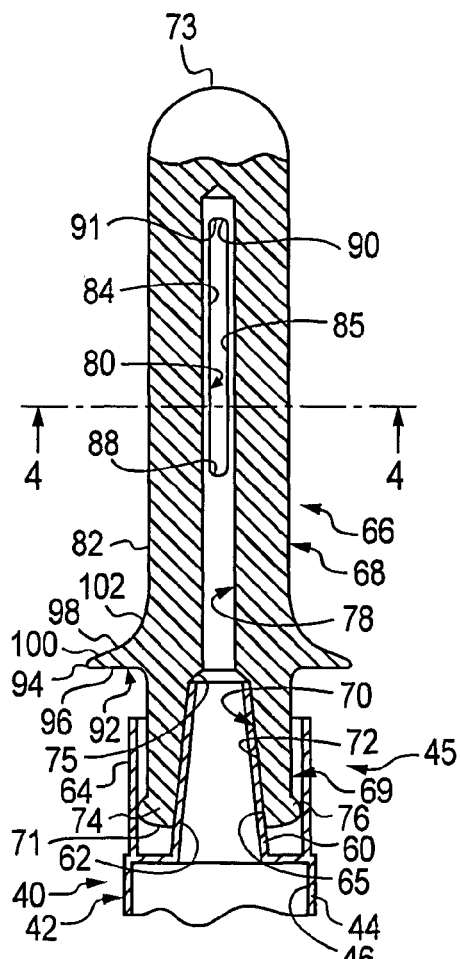
FIG. 2
FIG. 3

APPLICATOR FOR DISPENSING A MEDICINAL SUBSTANCE

This application is a continuation-in-part of (1) U.S. Application No. 13/064,467, filed on Mar. 29, 2011, which issued as U.S. Pat. No. 8,845,596, which is a continuation of (2) U.S. application Ser. No. 11/541,985, filed on Oct. 2, 2006, now abandoned, which is a division of (3) U.S. application Ser. No. 10/446,739, filed on May 28, 2003, which issued as U.S. Pat. No. 7,125,394, on Oct. 29, 2006, which is a continuation-in-part of (4) U.S. application Ser. No. 10/160,166, filed on Jun. 4, 2002, which issued as U.S. Pat. No. 7,141,036 on Nov. 28, 2006. The above-noted U.S. Applications (1) through (4) are incorporated herein by reference thereto.

BACKGROUND OF THE INVENTION

This invention relates to an applicator for dispensing a medicinal substance, and to methods associated therewith. This invention particularly relates to an applicator for readily dispensing a medicinal substance such as, for example, medicinal cream, compound, or the like, from the applicator. This invention further particularly relates to methods of making the applicator, and to methods of preparing a syringe/applicator assembly, for readily dispensing the medical substance from the applicator.

Frequently, various medical conditions exist within affected areas of openings of the human body, such as, for example, (1) natural openings of the anatomy of the human body including, but not limited to, the vaginal opening and the anal opening, and (2) non-natural openings such as surgically-formed openings, and/or openings resulting from injury. All of the above-noted openings are hereinafter referred to as "body openings." These medical conditions can be treated with medicinal creams and other substances of similar consistency. Frequently, such creams are prescribed by physicians, and are to be applied to tissue within the body openings over a period of time.

Because of the necessity for frequent applications of the cream to the affected areas, it is beneficial and economical for the patient to self-administer the medicinal cream. However, the cream may be applied by caregivers other than the patient.

In the past, techniques and devices have been developed to facilitate the dispensing of the cream generally within the body openings, but have tended not to be formed with structure which dispenses an ample amount of the cream onto the affected areas for a most effective treatment.

Thus, there is a need for a cream-delivery device, such as an applicator or a tip (both hereinafter referred to as "the applicator"), which facilitates the dispensing of an ample amount of medicinal cream onto tissue of the affected areas to be treated. Also, there is a need for a cream-delivery device, such as the applicator, which facilitates extension of the dispensing of the medicinal cream axially beyond a through slot of the applicator.

SUMMARY OF THE INVENTION

It is, therefore, an object of this invention to provide an applicator which facilitates the dispensing of an ample amount of a substance onto tissue surfaces to be treated.

Another object of this invention is to provide an applicator which facilitates extension of the dispensing of a substance axially beyond a through slot of the applicator.

With these and other objects in mind, this invention contemplates an applicator for dispensing a substance therethrough, which includes a body formed (1) about an axis which extends from a proximal end of the body to an exterior axial surface of a closed distal end of the body, and (2) with a proximal section which extends from the proximal end of the body toward the closed distal end of the body, and to a distal end of the proximal section. The proximal section of the body is formed with an axial entry passage extending through the proximal section from a the proximal end of the body toward a the closed distal end of the body, and to a distal end of the axial entry passage, which is formed with a prescribed diameter at the proximal end of the body. The body is formed with an axial intermediate passage having a proximal end in communication with the distal end of the axial entry passage, which extends toward the closed distal end of the body, and to a distal end of the axial intermediate passage, with the axial intermediate passage being formed with a uniform passage diameter which is less than the prescribed diameter. The body is formed about the axis thereof with a passage section, having a uniform exterior diameter, which extends from a proximal end thereof toward the closed distal end of the body, and to a distal end of the passage section. The passage section of the body fully surrounds at least a portion of the axial intermediate passage to the distal end of the axial intermediate passage. The body is formed about the axis thereof with a slot section, having the uniform exterior diameter, which extends from a proximal end of the slot section toward the closed distal end of the body, and to a distal end of the slot section, with the proximal end thereof being formed integrally with the distal end of the passage section. A slot delivery passage is formed axially through the slot section of the body from a proximal end thereof toward the closed distal end of the body, and to a closed distal end of the slot delivery passage, with the proximal end of the slot delivery passage being in communication with the distal end of the axial intermediate passage. At least one axially-elongated slot is formed radially through the slot section of the body in unobstructed communication with the axial slot delivery passage and an external surface of the body, and extends from the proximal end of the slot section toward the distal end of the slot section, and to a distal end of the at least one axially-elongated slot. The slot delivery passage is formed with the uniform passage diameter interrupted only by the presence of the at least one axially-elongated slot, which is formed with an extended side wall extending axially from a proximal end to the distal end of the at least one elongated slot. The extended side wall is located at one side of the at least one elongated slot, and extends from an inboard juncture of the extended side wall with the slot delivery passage to an outboard juncture of the extended side wall with the external surface of the body. A flat surface is formed in the body adjacent the at least one elongated slot, and has a first end spaced from the extended side wall. The flat surface extends from the first end thereof angularly away from the extended side wall to a second end of the flat surface at a juncture with the external surface of the body, and extends axially along at least a portion of the at least one elongated slot.

This invention further contemplates an applicator for dispensing a substance therethrough, which includes a body formed (1) about an axis which extends from a proximal end of the body to an exterior axial surface of a closed distal end of the body, and (2) with a proximal section which extends from the proximal end of the body toward the closed distal end of the body, and to a distal end of the proximal section. The proximal section of the body is formed with an axial entry passage extending through the proximal section from a the proximal end of the body toward a the closed distal end of the body, and to a distal end of the axial entry passage, which is formed with a prescribed diameter at the proximal end of the body. The body is formed with an axial intermediate passage having a proximal end in communication with the distal end of the axial entry passage, which extends toward the closed distal end of the body, and to a distal end of the axial intermediate passage, with the axial intermediate passage being formed with a uniform passage diameter which is less than the prescribed diameter. The body is formed about the axis thereof with a passage section, having a uniform exterior diameter, which extends from a proximal end thereof toward the closed distal end of the body, and to a distal end of the passage section. The passage section of the body fully surrounds at least a portion of the axial intermediate passage to the distal end of the axial intermediate passage. The body is formed about the axis thereof with a slot section, having the uniform exterior diameter, which extends from a proximal end of the slot section toward the closed distal end of the body, and to a distal end of the slot section, with the proximal end thereof being formed integrally with the distal end of the passage section. A slot delivery passage is formed axially through the slot section of the body from a proximal end thereof toward the closed distal end of the body, and to a closed distal end of the slot delivery passage, with the proximal end of the slot delivery passage being in communication with the distal end of the axial intermediate passage. At least one axially-elongated slot is formed radially through the slot section of the body in unobstructed communication with the axial slot delivery passage and an external surface of the body, and extends from the proximal end of the slot section toward the distal end of the slot section, and to a distal end of the at least one axially-elongated slot. The slot delivery passage is formed with the uniform passage diameter interrupted only by the presence of the at least one axially-elongated slot, which is formed with an extended side wall extending axially from a proximal end to the distal end of the at least one elongated slot. The extended side wall is located at one side of the at least one elongated slot, and extends from an inboard juncture of the extended side wall with the slot delivery passage to an outboard juncture of the extended side wall with the external surface of the body. An abbreviated side wall is formed in the applicator, spaced from the extended side wall, and extending from an inboard juncture of the abbreviated side wall with the slot delivery passage toward the external surface of the body, and to an outboard end of the abbreviated side wall spaced inward from the external surface of the body.

This invention further contemplates an applicator for dispensing a substance therethrough, which includes a body formed (1) about an axis which extends from a proximal end of the body to an exterior axial surface of a closed distal end of the body, and (2) with a proximal section which extends from the proximal end of the body toward the closed distal end of the body, and to a distal end of the proximal section. The proximal section of the body is formed with an axial entry passage extending through the proximal section from a the proximal end of the body toward a the closed distal end of the body, and to a distal end of the axial entry passage, which is formed with a prescribed diameter at the proximal end of the body. The body is formed with an axial intermediate passage having a proximal end in communication with the distal end of the axial entry passage, which extends toward the closed distal end of the body, and to a distal end of the axial intermediate passage, with the axial intermediate passage being formed with a uniform passage diameter which is less than the prescribed diameter. The body is formed about the axis thereof with a passage section, having a uniform exterior diameter, which extends from a proximal end thereof toward the closed distal end of the body, and to a distal end of the passage section. The passage section of the body fully surrounds at least a portion of the axial intermediate passage to the distal end of the axial intermediate passage. The body is formed about the axis thereof with a slot section, having the uniform exterior diameter, which extends from a proximal end of the slot section toward the closed distal end of the body, and to a distal end of the slot section, with the proximal end thereof being formed integrally with the distal end of the passage section. A slot delivery passage is formed axially through the slot section of the body from a proximal end thereof toward the closed distal end of the body, and to a closed distal end of the slot delivery passage, with the proximal end of the slot delivery passage being in communication with the distal end of the axial intermediate passage. At least one axially-elongated slot is formed radially through the slot section of the body in unobstructed communication with the axial slot delivery passage and an external surface of the body, and extends from the proximal end of the slot section toward the distal end of the slot section, and to a distal end of the at least one axially-elongated slot. The slot delivery passage is formed with the uniform passage diameter interrupted only by the presence of the at least one axially-elongated slot, which is formed with an extended side wall extending axially from a proximal end to the distal end of the at least one elongated slot. The extended side wall is located at one side of the at least one elongated slot, and extends from an inboard juncture of the extended side wall with the slot delivery passage to an outboard juncture of the extended side wall with the external surface of the body. An abbreviated side wall is formed in the applicator, spaced from the extended side wall, and extending from an inboard juncture of the abbreviated side wall with the slot delivery passage toward the external surface of the body, and to an outboard end of the abbreviated side wall spaced inward from the external surface of the body. A first end of a flat surface is joined with the abbreviated side wall at the outboard end thereof and extends away from the extended side wall.

This invention also contemplates an applicator for dispensing a substance therethrough, which includes a body formed (1) about an axis which extends from a proximal end of the body to an exterior axial surface of a closed distal end of the body, and (2) with a proximal section which extends from the proximal end of the body toward the closed distal end of the body, and to a distal end of the proximal section. The proximal section of the body is formed with an axial entry passage extending through the proximal section from the proximal end of the body toward a the closed distal end of the body, and to a distal end of the axial entry passage, which is formed with a prescribed diameter at the proximal end of the body. The body is formed with an axial intermediate passage having a proximal end in communication with the distal end of the axial entry passage, which extends toward the closed distal end of the body, and to a distal end of the axial intermediate passage, with the axial intermediate passage being formed with a uniform passage diameter which is less than the prescribed diameter. The body is formed about the axis thereof with a passage section, having a uniform exterior diameter, which extends from a proximal end thereof toward the closed distal end of the body, and to a distal end of the passage section. The passage section of the body fully surrounds at least a portion of the axial intermediate passage to the distal end of the axial intermediate passage. The body is formed about the axis thereof with a slot section, having the uniform exterior diameter, which extends from a proximal end of the slot section toward the closed distal end of the body, and to a distal end of the slot section, with the proximal end thereof being formed integrally with the distal end of the passage section. A slot delivery passage is formed axially through the slot section of the body from a proximal end thereof toward the closed distal end of the body, and to a closed distal end of the slot delivery passage, with the proximal end of the slot delivery passage being in communication with the distal end of the axial intermediate passage. At least one axially-elongated slot is formed radially through the slot section of the body in unobstructed communication with the axial slot delivery passage and an external surface of the body, and extends from the proximal end of the slot section toward the distal end of the slot section, and to a distal end of the at least one axially-elongated slot. The slot delivery passage is formed with the uniform passage diameter interrupted only by the presence of the at least one axially-elongated slot. The body is formed with an axially solid portion which extends distally from a distal end of the slot to the distal end of the body. A cleft is formed in at least a portion of an external surface of the solid portion of the body, with the cleft extending from, and in communication with, the distal end of the slot toward the distal end of the body. The cleft forms a structure which is angled outward as the cleft extends in a distal direction from a proximal end of the cleft to direct a medicinal substance exiting from the distal end of the at least one axially-extended slot to surfaces of a patient's tissue adjacent the cleft.

This invention also contemplates an applicator for dispensing a substance therethrough, which includes a body formed (1) about an axis which extends from a proximal end of the body to an exterior axial surface of a closed distal end of the body, and (2) with a proximal section which extends from the proximal end of the body toward the closed distal end of the body, and to a distal end of the proximal section. The proximal section of the body is formed with an axial entry passage extending through the proximal section from a the proximal end of the body toward a the closed distal end of the body, and to a distal end of the axial entry passage, which is formed with a prescribed diameter at the proximal end of the body. The body is formed with an axial intermediate passage having a proximal end in communication with the distal end of the axial entry passage, which extends toward the closed distal end of the body, and to a distal end of the axial intermediate passage, with the axial intermediate passage being formed with a uniform passage diameter which is less than the prescribed diameter. The body is formed about the axis thereof with a passage section, having a uniform exterior diameter, which extends from a proximal end thereof toward the closed distal end of the body, and to a distal end of the passage section. The passage section of the body fully surrounds at least a portion of the axial intermediate passage to the distal end of the axial intermediate passage. The body is formed about the axis thereof with a slot section, having the uniform exterior diameter, which extends from a proximal end of the slot section toward the closed distal end of the body, and to a distal end of the slot section, with the proximal end thereof being formed integrally with the distal end of the passage section. A slot delivery passage is formed axially through the slot section of the body from a proximal end thereof toward the closed distal end of the body, and to a closed distal end of the slot delivery passage, with the proximal end of the slot delivery passage being in communication with the distal end of the axial intermediate passage. At least one axially-elongated slot is formed radially through the slot section of the body in unobstructed communication with the axial slot delivery passage and an external surface of the body, and extends from the proximal end of the slot section toward the distal end of the slot section, and to a distal end of the at least one axially-elongated slot. The slot delivery passage is formed with the uniform passage diameter interrupted only by the presence of the at least one axially-elongated slot, which is formed with an extended side wall extending axially from a proximal end to the distal end of the at least one elongated slot. The extended side wall is located at one side of the at least one elongated slot, and extends from an inboard juncture of the extended side wall with the slot delivery passage to an outboard juncture of the extended side wall with the external surface of the body. A flat surface is formed in the body adjacent the at least one elongated slot, and has a first end spaced from the extended side wall. The flat surface extends from the first end thereof angularly away from the extended side wall to a second end of the flat surface at a juncture with the external surface of the body, and extends axially along at least a portion of the at least one elongated slot. The body is formed with an axially solid portion which extends distally from a distal end of the slot to the distal end of the body. A cleft is formed in at least a portion of an external surface of the solid portion of the body, with the cleft extending from, and in communication with, the distal end of the slot toward the distal end of the body. The cleft forms a structure which is angled outward as the cleft extends in a distal direction from a proximal end of the cleft to direct a medicinal substance exiting from the distal end of the slot to surfaces of a patient's tissue adjacent the cleft.

As further contemplated by this invention, an applicator includes a body having a stem formed with a common external surface. A slot delivery passage is formed axially through at least a portion of the stem, and a slot is formed through a portion of the stem from the slot delivery passage to the common external surface to facilitate the flow of a substance from within the slot delivery passage, through the slot, and to an environment adjacent the common external surface. The slot is formed with an extended side wall which extends axially from a proximal end to the distal end of the slot. The extended side wall is located at one side of the slot, and extends from an inboard juncture of the extended side wall with the slot delivery passage to an outboard juncture of the extended side wall with the common external surface of the stem. A flat surface is formed in the stem adjacent the slot, has a first end spaced from the extended side wall, and extends from the first end thereof angularly away from the extended side wall to a second end of the flat surface at a juncture with the common external surface of the stem.

This invention further contemplates an applicator which includes a body having a stem formed with a common external surface. A slot delivery passage is formed axially through at least a portion of the stem, and a slot is formed through a portion of the stem from the slot delivery passage to the common external surface to facilitate the flow of a substance from within the slot delivery passage, through the slot, and to an environment adjacent the common external surface. The slot is formed with an extended side wall which extends axially from a proximal end to the distal end of the slot. The extended side wall is located at a first side of the slot, and extends from an inboard juncture of the extended side wall with the slot delivery passage to an outboard juncture of the extended side wall with the common external surface of the stem. An abbreviated side wall is formed in the stem, at a second side of the slot, is spaced from the extended side wall, and extends from an inboard juncture of the abbreviated side wall with the slot delivery passage toward the common external surface of the stem, and to an outboard end of the abbreviated side wall spaced inward from the common external surface of the stem.

Further, this invention contemplates an applicator which includes a body having a stem formed with a common external surface. A slot delivery passage is formed axially through at least a portion of the stem, and a slot is formed through a portion of the stem from the slot delivery passage to the common external surface to facilitate the flow of a substance from within the slot delivery passage, through the slot, and to an environment adjacent the common external surface. The slot is formed with an extended side wall which extends axially from a proximal end to the distal end of the slot. The extended side wall is located at a first side of the slot, and extends from an inboard juncture of the extended side wall with the slot delivery passage to an outboard juncture of the extended side wall with the common external surface of the stem. An abbreviated side wall is formed in the stem, at a second side of the slot, is spaced from the extended side wall, and extends from an inboard juncture of the abbreviated side wall with the slot delivery passage toward the external surface of the body, and to an outboard end of the abbreviated side wall spaced inward from the external surface of the body. A flat surface is formed in the stem adjacent the second side of the slot, has a first end spaced from the extended side wall, and extends from the first end thereof angularly away from the extended side wall to a second end of the flat surface at a juncture with the common external surface of the stem.

Also, this invention contemplates an applicator which includes a body having a stem formed with a common external surface. A slot delivery passage is formed axially through at least a portion of the stem, and a slot is formed through a portion of the stem from the slot delivery passage to the common external surface to facilitate the flow of a substance from within the slot delivery passage, through the slot, and to an environment adjacent the common external surface. The slot is formed with an extended side wall which extends axially from a proximal end to the distal end of the slot. The extended side wall is located at a first side of the slot, and extends from an inboard juncture of the extended side wall with the slot delivery passage to an outboard juncture of the extended side wall with the common external surface of the stem. The stem is formed with an axially solid portion which extends distally from a distal end of the slot to the distal end of the stem. A cleft is formed in at least a portion of an external surface of the solid portion of the stem, with the cleft extending from, and in communication with, the distal end of the slot toward the distal end of the stem. The cleft forms a structure which is angled outward as the cleft extends in a distal direction from a proximal end of the cleft to direct a medicinal substance exiting from the distal end of the slot to surfaces of a patient's tissue adjacent the cleft.

This invention further contemplates an applicator which includes a body having a stem formed with a common external surface. A slot delivery passage is formed axially through at least a portion of the stem, and a slot is formed through a portion of the stem from the slot delivery passage to the common external surface to facilitate the flow of a substance from within the slot delivery passage, through the slot, and to an environment adjacent the common external surface. The slot is formed with an extended side wall which extends axially from a proximal end to the distal end of the slot. The extended side wall is located at a first side of the slot, and extends from an inboard juncture of the extended side wall with the slot delivery passage to an outboard juncture of the extended side wall with the common external surface of the stem. A flat surface is formed in the stem adjacent the slot, and has a first end spaced from the extended side wall. The flat surface extends from the first end thereof angularly away from the extended side wall to a second end of the flat surface at a juncture with the common external surface of the stem, and extends axially along the slot. The stem is formed with an axially solid portion which extends distally from a distal end of the slot to the distal end of the stem. A cleft is formed in at least a portion of an external surface of the solid portion of the body, with the cleft extending from, and in communication with, the distal end of the slot toward the distal end of the stem. The cleft forms a structure which is angled outward as the cleft extends in a distal direction from a proximal end of the cleft to direct a medicinal substance exiting from the distal end of the slot to surfaces of a patient's tissue adjacent the cleft.

This invention further contemplates an applicator which includes a body having a stem formed with a common external surface. A slot delivery passage is formed axially through at least a portion of the stem, and a slot is formed through a portion of the stem from the slot delivery passage to the common external surface to facilitate the flow of a substance from within the slot delivery passage, through the slot, and to an environment adjacent the common external surface. The slot is formed with an extended side wall which extends axially from a proximal end to the distal end of the slot. The extended side wall is located at a first side of the slot, and extends from an inboard juncture of the extended side wall with the slot delivery passage to an outboard juncture of the extended side wall with the common external surface of the stem. A flat surface is formed in the stem adjacent the slot, and has a first end spaced from the extended side wall. The flat surface extends from the first end thereof angularly away from a mouth of the slot located at an intersection of the slot and the slot delivery passage, with the mouth extending between a first side thereof at the intersection and a second side thereof at the intersection, spaced from the first side, with a space between the first side and the second side defining an opening of the mouth at the intersection, and the first end of the flat surface located at the second side of the mouth, with the flat surface extending to the juncture with the common external surface.

As contemplated further by this invention, an applicator for dispensing a medicinal substance therethrough includes a body formed about an axis which extends from a proximal end of the body to an exterior axial surface of a closed distal end of the body. The body is formed with a proximal section which extends from the proximal end of the body toward the closed distal end of the body, and to a distal end of the proximal section. The proximal section of the body is formed with an axial entry passage extending through the proximal section from the proximal end of the body toward a the closed distal end of the body, and to a distal end of the axial entry passage, which is formed with a prescribed diameter at the proximal end of the body. The body is formed with an axial intermediate passage having a proximal end in communication with the distal end of the axial entry passage, with the passage extending toward the closed distal end of the body, and to a distal end of the axial intermediate passage. The axial intermediate passage is formed with a uniform passage diameter which is less than the prescribed diameter, and the body is formed about the axis thereof with a passage section, having a uniform exterior diameter, which extends from a proximal end thereof toward the closed distal end of the body, and to a distal end of the passage section. The passage section of the body full surrounds at least a portion of the axial intermediate passage to the distal end of the axial intermediate passage. The body is formed about the axis thereof with a slot section, having the uniform exterior diameter, which extends from a proximal end of the slot section toward the closed distal end of the body, and to a distal end of the slot section, with the proximal end thereof being formed integrally with the distal end of the passage section. A slot delivery passage is formed axially through the slot section of the body from a proximal end thereof toward the closed distal end of the body, and to a closed distal end of the slot delivery passage, with the proximal end of the slot delivery passage being in communication with the distal end of the axial intermediate passage. At least one slot is arranged in a helical path about an axis of the body and formed through the slot section of the body in unobstructed communication with the slot delivery passage and an external surface of the body, and extending from the proximal end of the slot section toward the distal end of the slot section, and to a distal end of the at least one slot, and the slot delivery passage is formed with the uniform passage diameter interrupted only by the presence of the at least one slot.

This invention also contemplates an applicator for dispensing a medicinal substance therethrough including a body formed about an axis with the body extending from a proximal end of the body to a distal end of the body, and a stem which forms an axial portion of the body. The stem is formed with a common external surface, and a slot delivery passage formed axially through at least a portion of the stem. A slot is formed through a portion of the stem from the slot delivery passage to the common external surface to facilitate the flow of the medicinal substance from within the slot delivery passage, through the slot, and to an environment adjacent the common external surface. The slot is arranged in a helical path about the axis of the body and formed through the slot section of the body in unobstructed communication with the slot delivery passage and the common external surface of the stem, and extending from the proximal end of the slot section toward the distal end of the slot section, and to a distal end of the slot. The slot delivery passage is formed with the uniform passage diameter interrupted only by the presence of the at least one slot.

This invention also contemplates an applicator for dispensing a medicinal substance therethrough, including a body formed about an axis with the body extending from a proximal end of the body to a distal end of the body. A stem forms an axial portion of the body, and is formed with a common external surface. A slot delivery passage is formed axially through at least a portion of the stem, with a slot formed through a portion of the stem from the slot delivery passage to the common external surface to facilitate the flow of the medicinal substance from within the slot delivery passage, through the slot, and to an environment adjacent the common external surface. The slot is formed with an extended side wall which extends axially from a proximal end to the distal end of the slot, with the extended side wall located at one side of the slot, and extending from an inboard juncture of the extended side wall with the slot delivery passage to an outboard juncture of the extended side wall with the common external surface of the stem. A flat surface is formed in the stem adjacent the slot, and has a first end spaced from the extended side wall. The flat surface extends from the first end thereof angularly away from the extended side wall to a second end of the flat surface at a juncture with the common external surface of the stem, with the flat surface and the extended side wall extending axially along at least a portion of the slot.

This invention further contemplates a cream delivery assembly for dispensing a medicinal substance therefrom, including a syringe having a barrel, a barrel passage, a plunger, and a first stem with a mating coupler having a first portion formed at a distal end of the syringe. The cream delivery assembly also includes an applicator with the mating coupler having a second portion thereof formed at a proximal end of the applicator. The syringe and the applicator are in assembly where the first portion of the mating coupler is in mating coupling with the second portion of the mating coupler. The applicator has a body formed about an axis with the body extending from a proximal end of the body to a distal end of the body. A second stem forms an axial portion of the body, and is formed with a common external surface. A slot delivery passage of the applicator is formed axially through at least a portion of the second stem, with the barrel passage of the syringe being in communication with the slot delivery passage. A slot is formed through a portion of the second stem from the slot delivery passage to the common external surface to facilitate the flow of the medicinal substance from within the slot delivery passage, through the slot, and to an environment adjacent the common external surface. The slot is formed with an extended side wall which extends axially from a proximal end to the distal end of the slot. The extended side wall is located at one side of the slot, and extends from an inboard juncture of the extended side wall with the slot delivery passage to an outboard juncture of the extended side wall with the common external surface of the stem. A flat surface is formed in the stem adjacent the slot, and has a first end spaced from the extended side wall, with the flat surface extending from the first end thereof angularly away from the extended side wall to a second end of the flat surface at a juncture with the common external surface of the stem, The flat surface and the extended side wall extend axially along at least a portion of the slot.

This invention further contemplates a cream delivery assembly for dispensing a medicinal substance therefrom, including a syringe having a barrel, a barrel passage, a plunger, and a first stem with a mating coupler having a first portion formed at a distal end of the syringe. The cream delivery assembly also includes an applicator with the mating coupler having a second portion thereof formed at a proximal end of the applicator. The syringe and the applicator are in assembly where the first portion of the mating coupler is in mating coupling with the second portion of the mating coupler. The applicator has a body formed about an axis with the body extending from a proximal end of the body to a distal end of the body. A second stem forms an axial portion of the body, and is formed with a common external surface. A slot delivery passage of the applicator is formed axially through at least a portion of the second stem, with the barrel passage of the syringe being in communication with the slot delivery passage. A slot is formed through a portion of the second stem from the slot delivery passage to the common external surface to facilitate the flow of the medicinal substance from within the slot delivery passage, through the slot, and to an environment adjacent the common external surface. The slot is formed with an extended side wall which extends axially from a proximal end to the distal end of the slot. The extended side wall is located at one side of the slot, and extends from an inboard juncture of the extended side wall with the slot delivery passage to an outboard juncture of the extended side wall with the common external surface of the stem. The stem is formed with an axially solid portion which extends distally from a distal end of the slot to the distal end of the stem. A cleft is formed in at least a portion of an external surface of the solid portion of the stem, with the cleft extending from, and in communication with, the distal end of the slot toward the distal end of the stem. The cleft forms a structure which is angled outward as the cleft extends in a distal direction from a proximal end of the cleft to direct the medicinal substance exiting from the distal end of the slot to surfaces of a patient's tissue adjacent the cleft.

This invention further contemplates a method of making an applicator, including the steps of forming a body having a stem with a slot delivery passage and a common external surface, forming a slot in and extending through the stem from the slot delivery passage to the common external surface, with the slot having a side, and forming a flat surface having an inboard end at the side of the slot with the flat surface extending angularly away from the side towards the common external surface.

This invention also contemplates a method of making an applicator, including the steps of forming a body having a stem with a slot delivery passage and a common external surface, forming the slot to extend axially along a length of the slot from a proximal end of the slot to a distal end of slot; and forming a trough-like cleft in the common external surface of the stem adjacent and contiguous with the distal end of the slot.

This invention further contemplates a method of loading a substance into a cartridge, including the steps of providing the cartridge having an axial passage therethrough, inserting a plunger into the axial passage from a proximal end of the cartridge, positioning the plunger at a prescribed location within the axial passage to establish between the distal end of the plunger and the distal end of the cartridge a prescribed volume within the axial passage for receipt of a prescribed amount of the substance, and depositing the substance into the passage through an opening at the distal end of the cartridge and through the axial passage to the distal end of the plunger to provide the prescribed amount of the substance within the axial passage.

This invention also contemplates a method of loading a substance into a cartridge, including the steps of providing the cartridge having an axial passage therethrough, inserting a plunger into the axial passage from a proximal end of the cartridge, locating the plunger at a distal end of the cartridge within the axial passage, depositing a prescribed amount of the substance into the axial passage through an opening at the distal end of the cartridge, and moving the plunger toward the proximal end of the cartridge by a force of the prescribed amount of the substance being deposited into the axial passage.

This invention further contemplates a method of making a cream delivery assembly, including the steps of providing a syringe having a barrel, a barrel passage, a plunger, and a slidable stem having portions axially movable within the barrel passage from a proximal end of the syringe, forming a first portion of a mating coupler at a distal end of the syringe, providing an applicator having a body with a fixed stem of the body and a slot delivery passage formed axially in the stem, forming a slot in the body which communicates with the slot delivery passage and an environment externally of the body, forming a second portion of the mating coupler at a proximal end of the applicator, forming a flat surface in the stem adjacent a side of the slot which extends angularly away from the slot, and assembling the first portion of the mating coupler with the second portion of the mating coupler to couple the syringe to the applicator with the barrel passage of the syringe and the slot delivery passage of the applicator being in communication.

This invention also contemplates a method of making a cream delivery assembly including the steps of providing a syringe having a barrel, a barrel passage, a plunger, and a slidable stem having portions axially movable within the barrel passage from a proximal end of the syringe, forming a first portion of a mating coupler at a distal end of the syringe, providing an applicator having a body with a fixed stem of the body and a slot delivery passage formed axially in the stem, and a slot formed in the body which communicates with the slot delivery passage and an environment externally of the body, and having a second portion of the mating coupler formed at a proximal end of the applicator, providing the applicator with a solid portion of the stem at a distal end of the stem adjacent a distal end of the slot, forming a trough-like cleft in the solid portion of the stem contiguous with and adjacent a distal end of the slot, and assembling the first portion of the mating coupler with the second portion of the mating coupler to couple the syringe to the applicator with the barrel passage of the syringe and the slot delivery passage of the applicator being in communication.

BRIEF DESCRIPTION OF THE DRAWINGS

In the accompanying drawings:

FIG. 2 is a side view showing exterior structure of the first applicator;

FIG. 3 is an enlarged partial sectional view showing a proximal end of the first applicator in assembly with a distal end of the syringe of FIG. 1;

DETAILED DESCRIPTION OF THE INVENTION

Figure 1:
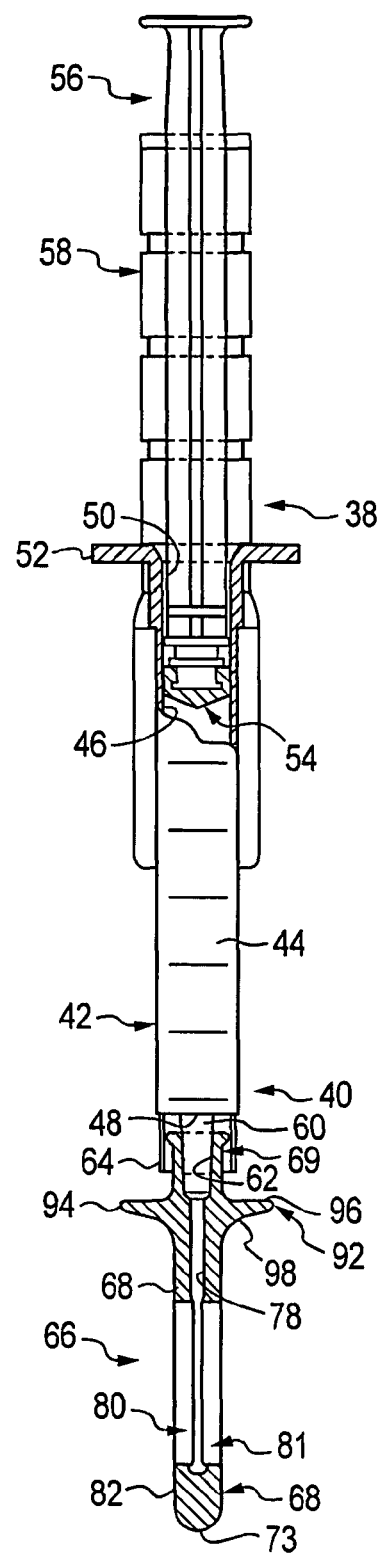
FIG. 1 is a partially-sectioned top view showing a focused dosimetry device, which is supporting a syringe, where a cartridge of the syringe is nested in a carrier of the device having spaced grooves for receiving a flange of the syringe, and further showing a first embodiment of an applicator ("first applicator"), in assembly with the syringe.

As noted above, various medical conditions frequently exist within affected tissue areas of openings of the human body, such as, for example, natural openings of the anatomy of the human body, including, but not limited to, the vaginal opening and the anal opening, and unnatural openings such as, for example, but not limited to, surgically-formed openings, and/or openings resulting from injury. Each of the above-noted natural and unnatural openings is hereinafter referred to as "a body opening."

Also, as noted above, the terms "applicator" and "tip" have been used interchangeably, in the past, to refer to a cream-dispensing component, of the type which is the subject of the invention described, claimed, and illustrated herein. For purposes of consistency in the description below, the term "applicator," will be used throughout, it being understood that such use also refers to the term "tip."

Further, various embodiments of applicators, to which this invention relates, and containers for storing a medicinal substance, to which the applicators are attachable, are described below, and are used to facilitate the dispensing of the medicinal substance, such as, for example, a medicinal cream, compound, or the like, (hereinafter referred to as "the cream"), onto affected tissue of body openings of a patient, when the applicators are located adjacent the tissue.

The consistency of the cream is such that the cream does not flow easily within or out of the containers without a force being applied to the stored mass thereof to move the cream from the containers into the respective applicator.

One example of a supply container for storing the medicinal substance is a rapid-delivery system, such as, for example, a piston-operable syringe, which can be used in conjunction with, or used without, a focused dosimetry device, as described below. A volume of the cream is deposited into a barrel of the syringe, and the applicator is attached to a distal or output end of the syringe. The syringe is operated in a conventional manner to force the cream from within the barrel, into the applicator, through slots of the applicator, and onto the affected tissue in body openings of the patient, which are adjacent outboard portions of the slots.

The volume of the cream deposited initially into the barrel of the cartridge can represent multiple doses of the cream, wherein several single doses can be administered successively through the applicator over a period of time. Alternatively, the volume of the cream deposited initially into the barrel of the cartridge can also represent sufficient cream for administering, through the applicator, a single dose only, rather than multiple doses.

Another example of a supply container for storing the cream is a squeeze tube, such as, for example, the type typically used to store toothpaste, and facilitate dispensing the toothpaste by squeezing the tube. The tube includes an enclosure formed by a flexible wall with a single outlet, which is sealed by a removable cap during periods when it is desired to retain the cream within the enclosure. When it is desired to urge the cream from within the enclosure of the tube, the cap is removed from the single outlet of the tube and the applicator is substituted therefor. By virtue of the flexible wall of the tube, the tube can be squeezed, pinched, or the like, to urge the cream from within the enclosure, through the single outlet, into the applicator, and through slots thereof to administer the cream onto the tissue within the body opening of the patient.

The various embodiments of the applicator, as described below, are particularly useful for applying and focusing each administered dose of the cream to affected tissue areas of vaginal and/or anal openings of the human anatomy, but can be used for applying and focusing the cream to tissue within any natural and/or non-natural body openings of the human body.

The below-described embodiments of the applicator include a first axial, or proximal, end, at which the cream enters the applicator, and a second axial, or distal, end spaced axially distally from the first axial end. The end of any structural portion, such as, for example, an axially extending slot, of each of the various embodiments of the applicator, which is closest to the proximal end of the applicator, will be referred to as the proximal end of such structural portion, and the other end of such structural portion or applicator, which is opposite the proximal end, will be referred to as the distal end. For example, an axially extended slot formed radially through the applicator will extend between a proximal end and a distal end thereof.

Figure 6:
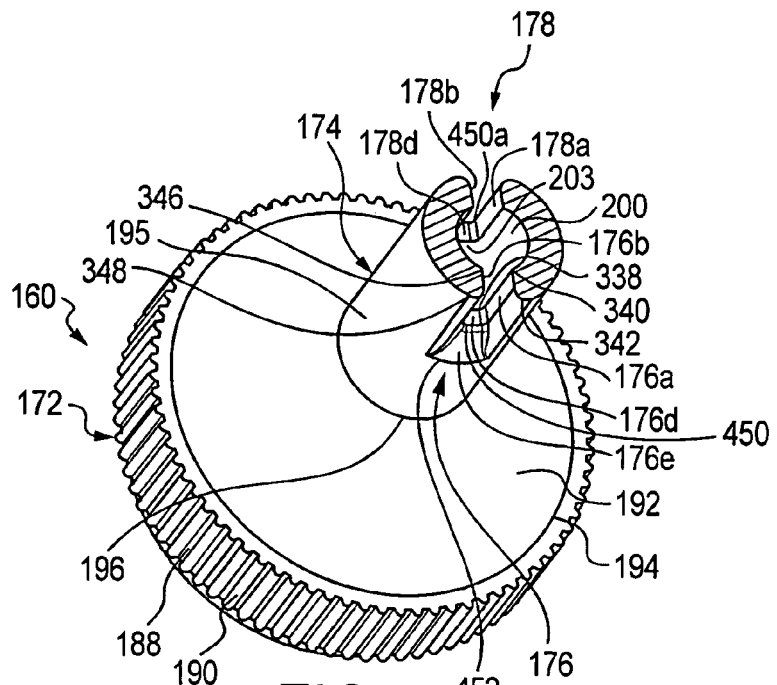
FIG. 6 is a partially-sectioned, perspective view showing a portion of the second applicator of FIG. 5 with the slot section of the body thereof being sectioned to show interior structure of the body and the two slots, in accordance with certain principles of the invention.
Figure 6A:
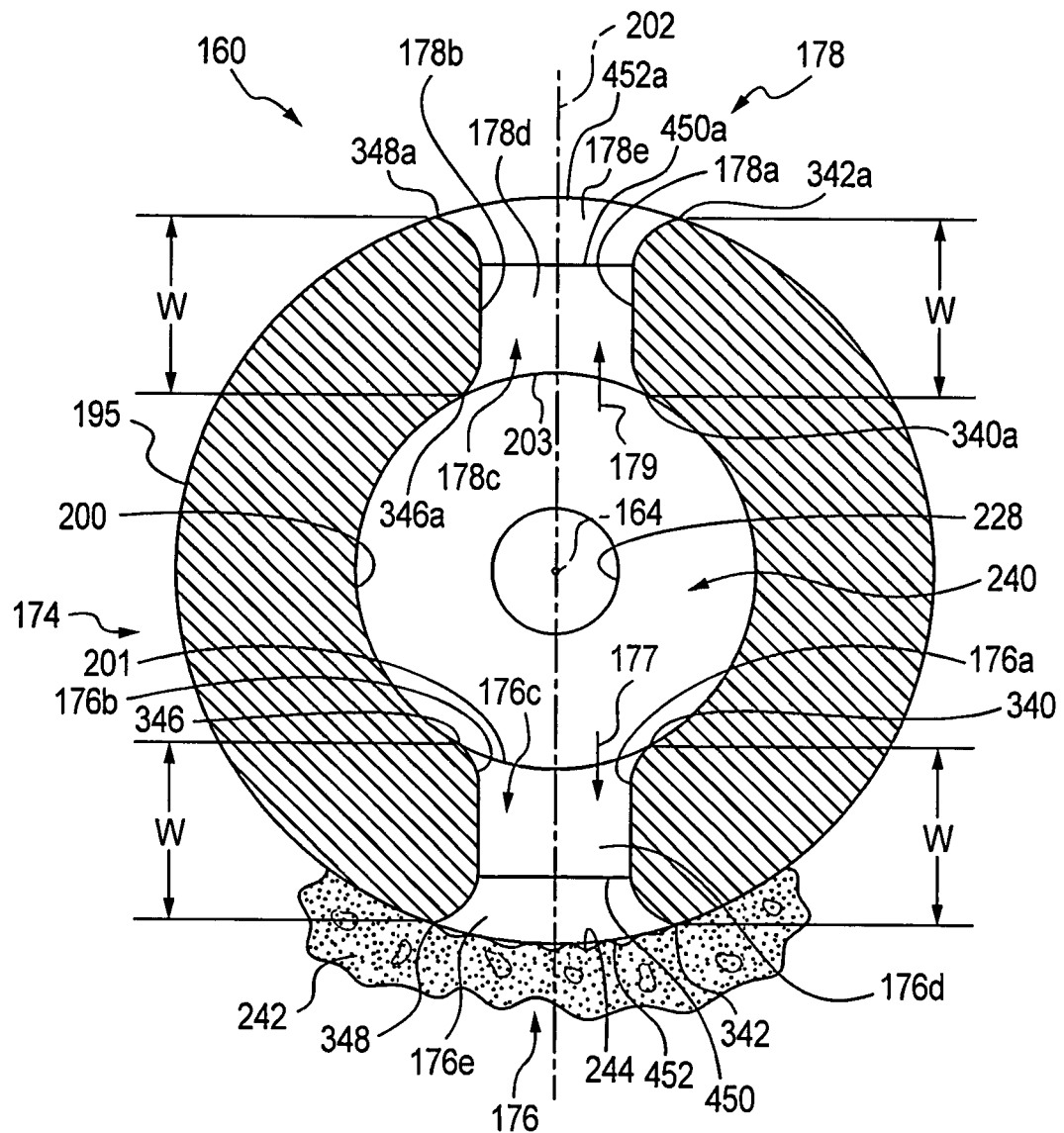
FIG. 6a is an enlarged sectional view, taken along line 6a-6a of FIG. 5, showing a dimensional relationship of two interfacing side walls of each of the two slots of the body of the second applicator of FIG. 5, with the flange extracted from the sectional view for clarity purposes, and further showing a first embodiment of respective junctures between end walls at opposite ends of each slot and transitional surfaces, each of which slope to a common outer surface of the body, in accordance with certain principles of the invention.
Figure 12:
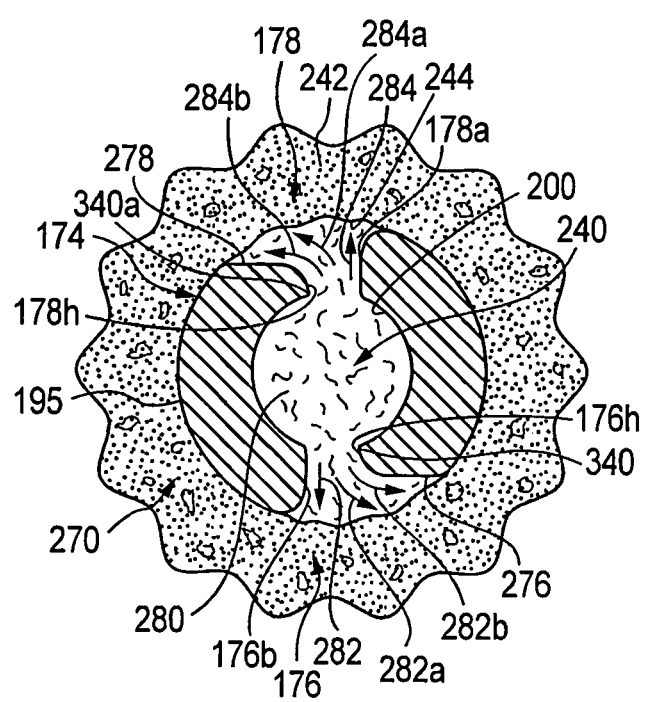
FIG. 12 is a sectional view showing the slot section of the third applicator located within a body opening of a patient, and the manner in which medicinal cream is applied to tissue within the body opening relative to the openings of the two slots and the respective flat surfaces thereof, in accordance with certain principles of the invention.

As shown in FIGS. 6*a* and 12, a cream 280 is being applied onto selected surfaces of the tissue 242 within a body opening 244 of a patient.

Referring to FIG. 1, a first technique for applying the cream 280 (FIGS. 6*a* and 12) to the surfaces of the tissue 242 could include the use of a focused dosimetry device 38, which is typically used in multiple dose applications, but can be used solely for single dose applications. The device 38 can support, and is used with, a syringe 40, which includes a cartridge 42 having a barrel 44. The syringe 40 serves as a rapid-delivery, cream-supply container for storing the cream 280 therein, or storing any other substance having a cream-like consistency.

In the syringe 40, the barrel 44 is formed with a hollow interior barrel passage 46, having a distal opening 48 at a distal end thereof and a proximal opening 50 at a proximal end thereof. A flange 52 is formed radially outward on the barrel 44 at the proximal end thereof. The syringe 40 further includes a plunger 54, which is located within the barrel passage 46, and a stem 56, which is insertable into the proximal opening 50. This structural arrangement facilitates movement of the plunger 54 within the barrel passage 46 toward the distal opening 48 thereof, to dispense the cream 280 externally from within the barrel passage, at the distal end of the cartridge 42.

The device 38 includes a carrier 58, which supports the cartridge 42 and the stem 56 during use of the device, and, in conjunction with the flange 52 of the barrel 44, facilitates the dispensing of successive single-dose applications, or a single dose only, of the cream 280 from the barrel.

A more detailed description of the structure and the operation of the device 38, in conjunction with the syringe 40, is described in U.S. Pat. No. 7,125,394, which, as noted above, is incorporated herein by reference thereto.

In the syringe 40, a small-diameter sleeve 60 forms an integral part of the cartridge 42, is in axial alignment with the barrel 44 at the distal end thereof, and forms a sleeve passage 62, which is in communication with the barrel passage 46. The exterior of the small-diameter sleeve 60 is tapered in the form of a frustum, with the smaller diameter of the frustum located at the distal end of the sleeve, and the axis of the frustum being coincidental with the axis of the barrel 44.

A large-diameter sleeve 64 also forms an integral part of the cartridge 42, at the distal end thereof, and is in axial alignment with the barrel 44, and in coaxial alignment with, and about, the small-diameter sleeve 60. An internal cylindrical wall of the large-diameter sleeve 64 can be threaded or unthreaded, and the proximal end of the large-diameter sleeve is closed (FIG. 3) and not in communication with the barrel passage 46.

Referring to FIGS. 1, 2, and 3, a first embodiment of an applicator 66 (hereinafter "the first applicator 66") has a body 68, which, as shown in FIG. 3, is formed with a proximal coupler 69 having an axial entry passage 70 therein. The first applicator 66 is assembled with the cartridge 42 at the distal end of the barrel 44, for example, by use of a known coupling facility 45 such as the coupling facility associated with U.S. Registered Trademark LUER-LOK, which is owned by Becton, Dickinson and Company, having an office in Franklin Lakes, N.J.

In particular, as shown in FIG. 3, the axial entry passage 70 of the first applicator 66 is formed with a tapered wall 72 which tapers axially inward from a proximal end of the passage to a distal end thereof, and which mates with the exterior taper of the sleeve 60 of the cartridge 42 to facilitate one aspect of the attachment of the applicator with the cartridge. The axial entry passage 70, which is formed with a prescribed diameter at a proximal end 71 of the body 68, extends from the proximal end of the body 68 toward a distal end 73 of the body and to a distal end 75 of the axial entry passage. The body 68 of the first applicator 66 is formed within a first ear 74 and a second ear 76, which extend outward in radially opposite directions from the proximal end of the first applicator.

Upon assembly of the first applicator 66 with the cartridge 42, the outboard ends of the ears 74 and 76 are threadedly, or frictionally, applied to, and within, the large-diameter sleeve 64 by rotation of the first applicator. The rotation of the first applicator 66 also enhances the tapered assembly of the tapered small-diameter sleeve 60 with the tapered proximal opening 72 of the axial entry passage 70.

It is noted that facilities, other than as described above, can be used to attach the first applicator 66 to the cartridge 42 without departing from the spirit and scope of the invention. Such attachment facilities could be threaded, unthreaded, tapered, press fit, or the like. The threaded attachment facilities include, but are not limited to, the facilities described below, and illustrated in FIGS. 18, 19, and 20.

As further shown in FIG. 3, the first applicator 66 is also formed with an inner axial delivery passage 78, which extends axially of the body 68, with a uniform diameter, between an open proximal end 75 and a closed distal end 90 of the axial delivery passage. The axial entry passage 70 is in communication with the axial delivery passage 78, with the distal end of the axial entry passage and the proximal end of the axial delivery passage being located at the transaxial juncture of the passages. In the first applicator 66, the uniform diameter of the axial delivery passage 78 is less than the prescribed diameter of the axial entry passage 70 at the proximal, or entry, end 71 of the passage 70.

The axial entry passage 70 could be formed in a configuration other than the tapered wall. The uniform diameter of the axial delivery passage 78 is less than the prescribed diameter of the axial entry passage 70 at the proximal, or entry, end 71 of the axial entry passage.

A pair of diametrically-opposed axially extending, elongated slots 80 (FIG. 3) and 81 (FIG. 2) are formed in the body 68. Each of the slots 80 and 81 are in communication with, and extend radially through the body 68 from the axial delivery passage 78 and exit at smooth exterior surfaces 82 on opposite sides of the body, adjacent exterior portions of the slots. As shown in FIG. 3, the slot 80 is formed with spaced, axially-extending, interfacing side walls 84 and 85, which extend from a proximal end 88 of the slot to a distal end 91 thereof, and define the width of the slot.

In similar fashion, the slot 81 (FIG. 2) is formed with spaced, axially-extending side walls, which extend from a proximal end of the slot 81 to a distal end thereof, and define the width of the slot. The axial entry passage 70, the axial delivery passage 78, and the slots 80 and 81 are all in communication with each other to facilitate the smooth flow of the cream 280 from the barrel 44 and through the first applicator 66 to locations externally of the first applicator. It is noted that, while the above-described first applicator 66 includes the pair of slots 80 and 81, the first applicator could be formed with a single slot, or more than two slots, all without departing from the spirit and scope of the invention.

Referring further to FIG. 3, the first applicator 66 is formed with a tactile-indicating flange 92 near the proximal end 71 thereof. The applicator body 68 is formed with the smooth exterior surface 82 of a uniform external diameter, and extends from the flange 92 nearly to the distal end 73 of the body, and is interrupted only by the openings of the slots 80 and 81 formed in the exterior surface.

The flange 92 extends radially outward from the exterior surface 82 of the body 68 to an outer edge surface 94 of the flange. The flange 92 is formed with a proximal surface 96 facing in a direction toward the proximal end 71 of the body 68 and a distal surface 98 facing in a direction toward the distal end 73 of the body. The distal surface 98 of the flange 92 is formed by a straight portion 100 which extends from the outer edge surface 94 of the flange, radially inward toward the axis of the body 68 and toward the distal end 73 of the body, to an inboard edge of the straight portion spaced radially outward from the external surface of the body. The distal surface 98 of the flange 92 is formed with a concave portion 102 which extends from the inboard edge of the straight portion toward the distal end 73, and to the external surface 82, of the body 68. The flange 92, with the concave portion 102 and the angled flat portion 100, provides a user-friendly tactile indication to the patient that the first applicator 66 has been inserted into body openings at the appropriate distance for placement of the slots 80 adjacent the tissue areas to be treated with the cream 280.

Figure 4:
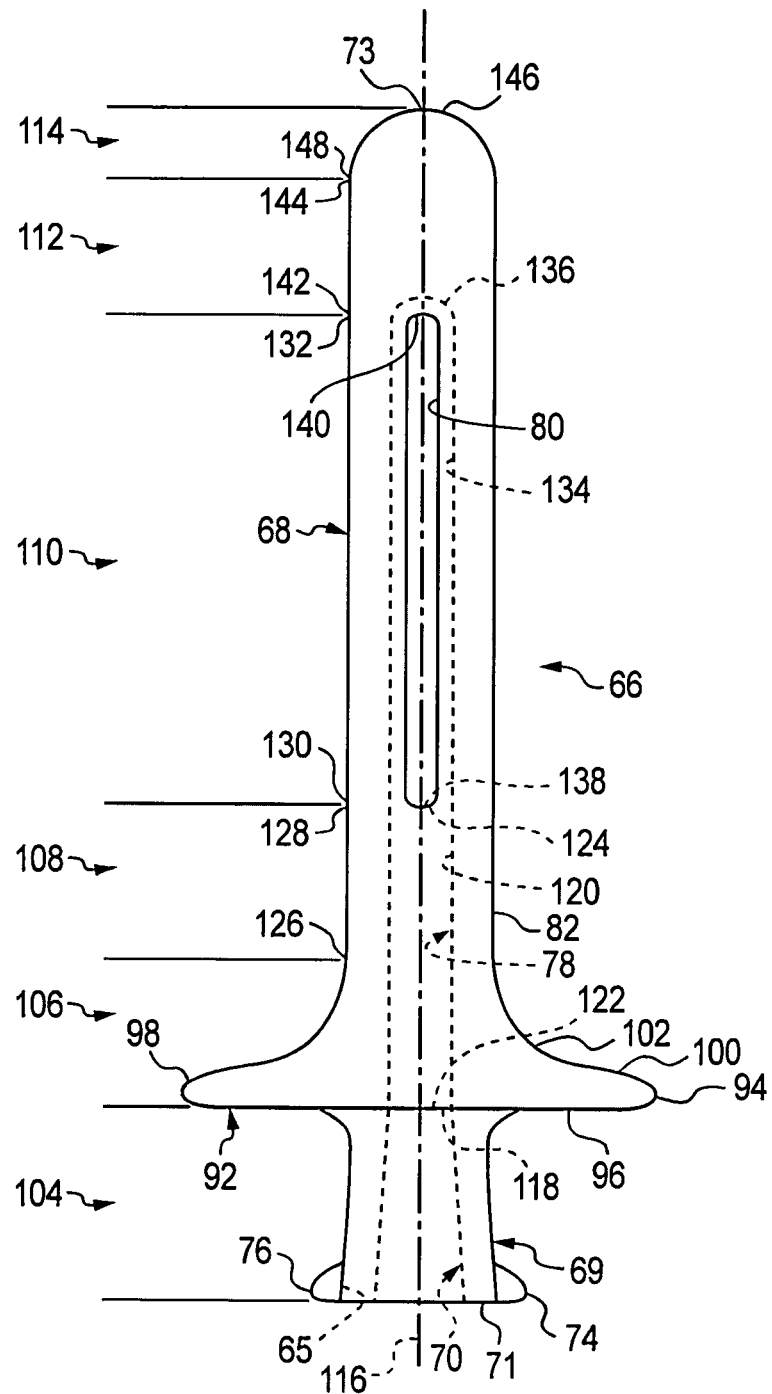
FIG. 4 is a side view showing the first applicator formed with integrally-joined sections.

Referring to FIG. 4, and in an alternative manner of describing the first applicator 66, which is also shown in FIGS. 1, 2 and 3, the first applicator includes the unitary body 68, formed by six integrally joined sections, identified as a proximal section 104, a flange section 106, a passage section 108, a slot section 110, a solid section 112, and a dome section 114.

As noted above, the first applicator 66 is designed to facilitate the dispensing of the cream 280 therethrough, where the cream has a consistency of the type which does not flow without a force being applied thereto.

The body 68 of the first applicator 66 is formed about an axis 116, which extends from the proximal end 71 of the body to the closed distal end 73 of the body.

The proximal section 104 of the body 68 is formed with the axial entry passage 70, which extends from the proximal end 71 of the body toward the closed distal end 73 of the body, and to a distal end 118 of the axial entry passage. The axial entry passage 70 is formed with a prescribed diameter, at least at the proximal end 71 of the body 68.

The body 68 is also formed with an axial intermediate passage 120 having a proximal end 122, which is coincidental with the distal end 118 of the axial entry passage 70. The axial intermediate passage 120 is formed with a uniform passage diameter, which is less than the prescribed diameter, and extends toward the closed distal end 73 of the body 68, and to a distal end 124 of the axial intermediate passage.

The body 68 is formed about the axis 116 thereof with the passage section 108, which has a uniform exterior diameter. The passage section 108 extends from a proximal end 126 thereof toward the closed distal end 73 of the body 68, and to a distal end 128 of the passage section, and fully surrounds at least a portion of the axial intermediate passage 120 to the proximal end 124 thereof.

The body 68 is formed about the axis 116 thereof within the slot section 110, and is formed with the uniform exterior diameter. The slot section 110 extends from a proximal end 130 thereof toward the closed distal end 73 of the body 68, and to a distal end 132 of the slot section, with the proximal end 130 of the slot section formed integrally with the distal end 128 of the passage section 108.

A slot delivery passage 134 is formed axially through the slot section 110 of the body 68 from the proximal end 130 of the slot section toward the closed distal end 73 of the body, and to a closed distal end 136 of the slot delivery passage, with a proximal end 138 of the slot delivery passage being in communication with the distal end 124 of the axial intermediate passage 120.

The axially-elongated slot 80 (hereinafter "the at least one axially-elongated slot 80") is formed radially through the slot section 110 of the body 68 in unobstructed radial communication with the slot delivery passage 134 and an exterior of the body, and extends from the proximal end 130 of the slot section toward the distal end 132 thereof, and to a distal end 140 of the at least one axially-elongated slot 80. The slot delivery passage 134 is formed with the uniform passage diameter, interrupted only by the presence of the at least one axially-elongated slot 80.

The body 68 is formed with the solid section 112, having the uniform exterior diameter, which extends from a closed proximal end 142 of the solid section toward the closed distal end 73 of the body, and to a closed distal end 144 of the solid section. The closed proximal end 142 of the solid section 112 is formed integrally with the distal end 132 of the slot section 110.

The body 68 is formed with the dome section 114 in the form of a solid dome 146, which extends from a closed proximal end 148 of the dome section to the closed distal end 73 of the body, with the closed proximal end being coincidental with the exterior axial surface of the dome. The closed proximal end 148 of the dome section 114 is formed integrally with the closed distal end 144 of the solid section 112. The solid section 112 and the dome section 114 are exclusive of any opening therethrough.

It is noted that the axial intermediate passage 120 of the passage section 108, and the slot delivery passage 134 of the slot section 110, are axially aligned and combine to form the axial delivery passage 78 as illustrated in FIG. 3. Further, as described above, and with reference to FIG. 4, the axially aligned axial intermediate passage 120 and the slot delivery passage 134 are formed with the uniform passage diameter.

As further shown in FIG. 4, the flange 92 is located in the flange section 106, between the proximal section 104 and the passage section 108. The flange 92 is integrally joined with adjacent portions of the body 68, at opposite axial ends of the flange, and fully radially surrounds a portion of the axial intermediate passage 120. Thus, except for the presence of the at least one axially-elongated slot 80, successive portions of the body 68, which are located in the three sections identified as the flange section 106, the passage section 108 and the slot section 110, surround the axial delivery passage 78 (FIG. 3), which, as noted above, is formed by the axial intermediate passage 120 and the slot delivery passage 134 illustrated in FIG. 4.

The exterior structure of the flange 92, as illustrated in FIG. 4, is described above with respect to FIG. 3, and is not further described herein.

With the structure of the body 68 as described above, there is full communication from an exterior of the body, at the proximal end 71 thereof, through the axial entry passage 70, the axial intermediate passage 120, the slot delivery passage 134, the at least one axially-elongated slot 80, and an exterior of the body adjacent the at least one axially-elongated slot.

Referring to FIGS. 5, 6, 6a, and 6b, a second embodiment of an applicator 160 (hereinafter "the second applicator 160") has an integrally-formed, unitary body 162, which extends axially along an axis, or centerline, 164 between a proximal end 166 and a closed distal end 168 of the body. The body 162 is formed integrally with (1) a proximal coupler 170 which extends axially from the proximal end 166 of the body, (2) an axially-elongated circular flange 172, (3) an axially-elongated stem 174 formed transaxially with two axially-elongated diametrically-spaced slots 176 and 178 (FIG. 6), (4) an axially-elongated solid spacer 180, and (5) an axially-elongated dome 182 which extends axially to the distal end 168 of the body.

A distal end of the proximal coupler 170 is joined integrally, at a juncture 184 (FIG. 6b), with a proximal side of the flange 172, and is formed with a cylindrical exterior surface 186 having a prescribed external diameter. The flange 172 is formed with a cylindrical exterior surface 188 having an external diameter which is greater than the prescribed external diameter. To facilitate manually-controlled rotation of the applicator 160, the perimeter of the exterior surface 188 of the flange 172 is formed with parallel, axially-aligned, spaced serrations, or splines, 190, which enhance manual gripping of the exterior surface of the flange.

The flange 172 is further formed with an external, concave, distal surface 192, which extends integrally between a distal edge 194 of the cylindrical exterior surface 188 and a juncture 196 of a distal end of the concave distal surface and a proximal end of the stem 174. The stem 174 and the solid spacer 180 are formed with a common external surface 195, having an external diameter, which is less than the prescribed external diameter. The stem 174 and the solid spacer 180 are integrally joined at a juncture 198 (FIG. 6b) of a distal end of the stem and a proximal end of the solid spacer. A distal end of the solid spacer 180 is integrally joined with a proximal end of the dome 182 at a juncture 199 (FIG. 6b) thereof. Also, the solid spacer 180 and the dome 182 are solid, and do not have any passages, slots, or the like formed therethrough.

Figure 6B:
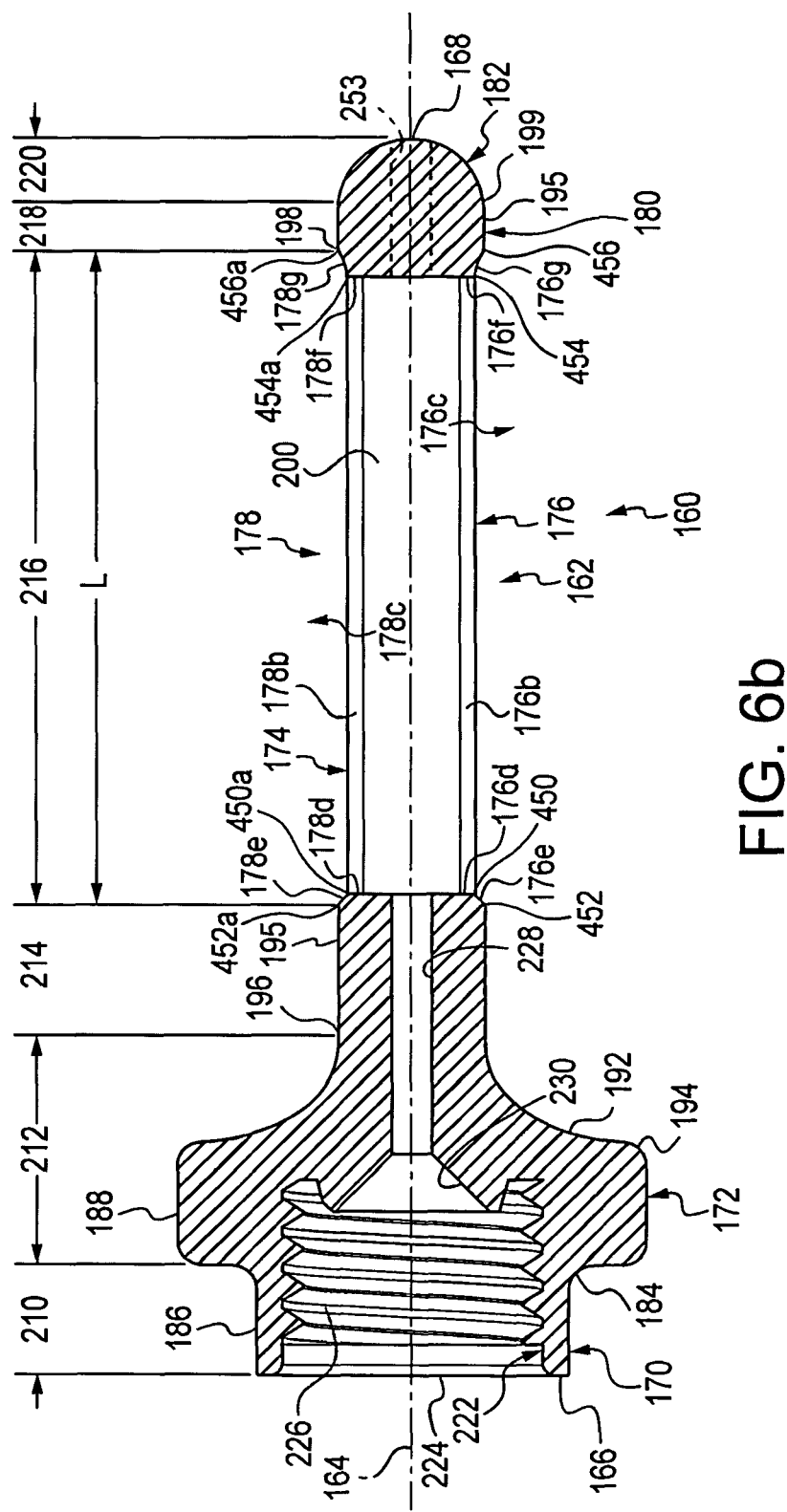
FIG. 6b is a sectional view, taken along line 6b-6b of FIG. 5, showing internal structure of the second applicator of FIG. 5 with integrally-joined sections thereof, and formed with axially-aligned, internal, communicating passages of different diameters, in accordance with certain principles of the invention.

Referring to FIGS. 6a and 6b, the stem 174 is formed axially with a slot delivery passage 200, having a prescribed internal diameter, which communicates with the axially-elongated slots 176 and 178. The slot 176 includes a first extended side wall 176a and a second extended side wall 176b, which are parallel to each other, and which define a space 176c, or confined passage, therebetween, for guiding the cream 280 (FIG. 12) therethrough in a direct outward flow path indicated by an arrow 177.

As shown in FIG. 6a, a transaxis, or centerline, 202 extends radially through, and from, the axis 164 and defines a transaxis plane. The extended side walls 176a and 176b are generally parallel to each other, and to the transaxis plane of the transaxis 202. However, each of the extended side walls could be formed at angles, other than being parallel, with respect to the transaxis plane, and/or each other, without departing from the spirit and scope of the invention.

A proximal wall 176d, or floor, is formed at a proximal end portion of the slot 176, and extends radially between (1) an arcing intersection 201 of a wall of the slot delivery passage 200 and the proximal wall, or floor, and (2) a distal straight-line juncture 450 of the proximal wall and a proximal transition surface 176e. Further, the proximal wall 176d is integrally joined at opposite sides with, and extends between, proximal ends of the spaced, first and second extended side walls 176a and 176b, respectively. The proximal transition surface 176e is formed in the common external surface 195, and slopes outward, in a proximal direction, from the distal juncture 450 to a proximal juncture 452 of the proximal transition surface with the common external surface.

Further, at the distal end of the slot 176 (FIG. 6b), the slot includes a distal end wall 176f, or floor, between the spaced, first and second extended side walls 176a and 176b, respectively, at the distal ends thereof. A distal transition surface 176g is formed in the common external surface 195 in a manner similar to the forming of the proximal transition surface 176e, except that the distal transition surface slopes radially outward, in a distal direction, from a proximal juncture 454 thereof with the distal wall 176f to a distal juncture 456 thereof with the common external surface.

Figure 5:
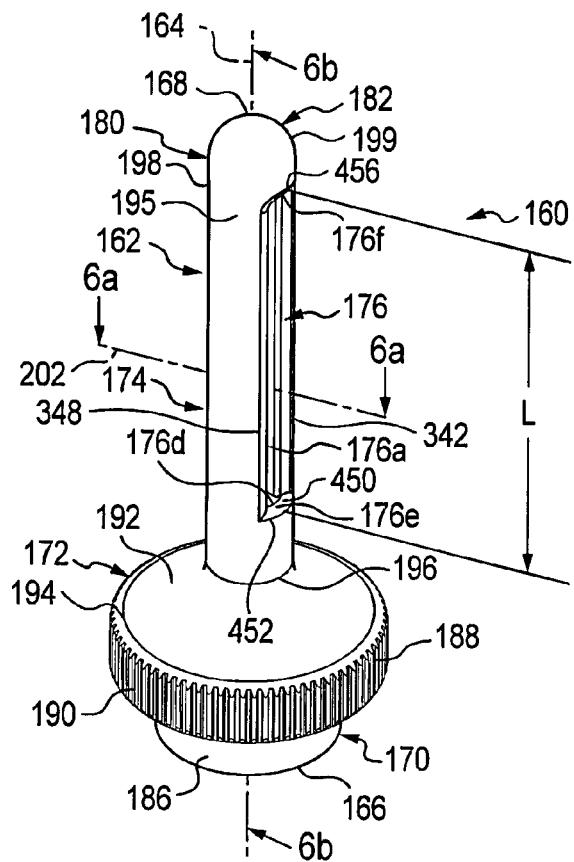
FIG. 5 is a perspective view showing a second embodiment of an applicator ("second applicator") formed with an axially-elongated, circular flange having a serrated or splined edge, and a generally cylindrical body, and further showing one of two diametrically-interfacing dispensing slots formed in a slot section, or stem, of the body, in accordance with certain principles of the invention.

As shown in FIGS. 5 and 6b, the slot 176 extends, by a distance "L," axially between the proximal juncture 452 of the proximal transition surface 176e and the common external surface 195, and the distal juncture 456 of the distal transition surface 176g with the common external surface. It is noted that the distal juncture 456 of the distal transition surface 176g is coincidental with the juncture 198 of the stem 174 and the solid spacer 180.

As shown in FIG. 6a, the first extended side wall 176a of the slot 176 is formed dimensionally with a width "W," which extends in a first direction from an integral junction 340 of the side wall with the slot delivery passage 200 to an integral junction 342 of the side wall with the common external surface 195. Also, the second extended side wall 176b of the slot 176 is formed dimensionally with the width "W," which extends in a second direction from an integral junction 346 of the side wall with the slot delivery passage 200 to an integral junction 348 of the side wall with the common external surface 195. In the applicator 160, the first direction, in which the first extended side wall 176a extends from the slot delivery passage 200, is generally parallel with the second direction, in which the second extended side wall 176b extends from the slot delivery passage. With this structural arrangement, the first and second extended side walls 176a and 176b, respectively, are generally parallel and spaced apart to define, along the axial length "L" of the slot 176, the outward flow path of the cream 280 through the slot, as indicated by the arrow 177.

Figure 11:
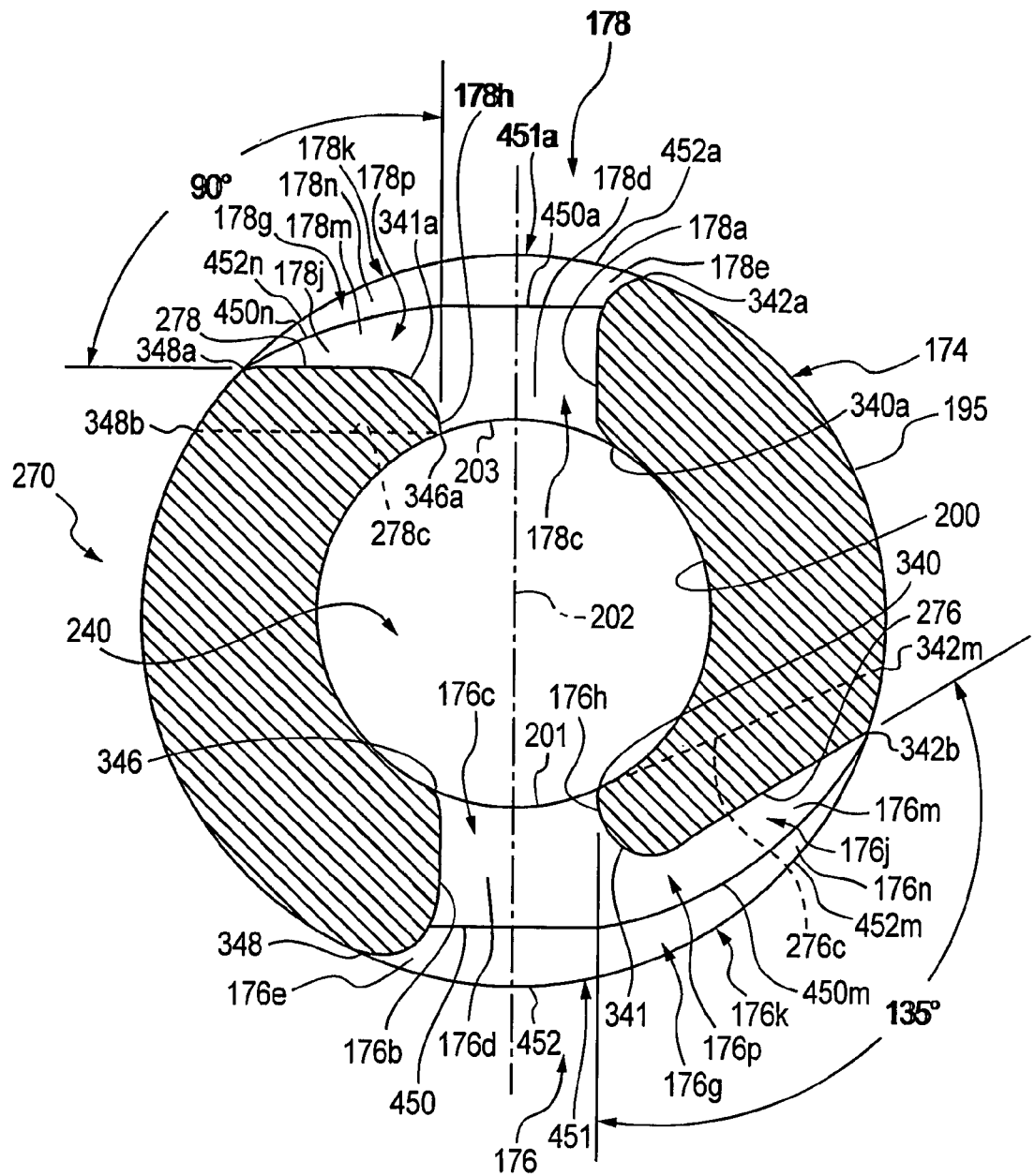
FIG. 11 is an enlarged view of the sectioned portion of the slot section of FIG. 10 showing different angular arrangements of the flat surface of each of the two slots relative to a respective adjacent side surface of each slot, and further showing a second embodiment of the juncture of FIG. 6a, in accordance with certain principles of the invention.

Referring to FIG. 11, the arcing intersection 201 defines a mouth of the slot 176, which extends between the integral juncture 340, representing a first side of the mouth, and the integral juncture 346, representing a second side of the mouth spaced from the first side of the mouth. A space is formed between the first side of the mouth and the second side of the mouth, which defines an opening of the mouth at the intersection.

In similar fashion, the slot 178 includes a first extended side wall 178a and a second extended side wall 178b, which define a space 178c, or confined passage, therebetween, for guiding the cream 280 (FIG. 12) therethrough in a direct outward flow path indicated by an arrow 179.

As shown in FIG. 6a, the extended side walls 178a and 178b are generally parallel to each other, and to the transaxis plane of the transaxis centerline 202. However, each of the extended side walls 178a and 178b could be formed at angles, other than being parallel, with respect to the transaxis plane, and/or each other, without departing from the spirit and scope of the invention.

A proximal wall 178d, or floor, is formed at a proximal end portion of the slot 178, and extends radially between (1) an arcing juncture 203 of the wall of the slot delivery passage 200 and the proximal wall, and (2) a distal straight-line juncture 450a of the proximal wall and a proximal transition surface 178e. Further, the proximal wall 178d is integrally joined at opposite sides with, and extends between, proximal ends of the spaced, first and second extended side walls 178a and 178b, respectively. The proximal transition surface 178e is formed in the common external surface 195, and slopes outward, in a proximal direction, from the distal juncture 450a to a proximal juncture 452a of the proximal transition surface with the common external surface.

Further, at a distal end of the slot 178, as shown in FIG. 6b, the slot 178 includes a distal end wall 178f, or floor, between the spaced, first and second extended side walls 178a and 178b, respectively. A distal transition surface 178g is formed in the common external surface 195 in a manner similar to the forming of the distal transition surface 178e, except that the distal transition surface slopes radially outward, in a distal direction, from a proximal juncture 454a thereof with the distal end wall 176f to a distal juncture 456a thereof with the common external surface.

As shown in FIG. 6b, the slot 178 extends, by the distance "L," axially between the proximal juncture 452a of the proximal transition surface 178e, and the distal juncture 456a of the distal transition surface 178g. It is noted that the distal juncture 456a of the distal transition surface 178g is coincidental with the juncture 198 of the stem 174 and the solid spacer 180.

As shown in FIG. 6a, the first extended side wall 178a of the slot 178 is formed dimensionally with the width "W," which extends from an integral junction 340a of the side wall with the slot delivery passage 200 to an integral junction 342a of the side wall with the common external surface 195. Also, the second extended side wall 178b of the slot 178 is formed dimensionally with the width "W," which extends from an integral junction 346a of the side wall with the slot delivery passage 200 to an integral junction 348a of the side wall with the common external surface 195. In the applicator 160, the first direction, in which the first extended side wall 178a extends from the slot delivery passage 200, is generally parallel with the second direction, in which the second extended side wall 178b extends from the slot delivery passage.

In this manner, each of the slots 176 and 178 provide a radial path for the travel of the cream 280 directly from the slot delivery passage 200, in opposite directions through the respective slots along the length "L" of the slots, and generally parallel to a slot centerline 202, to the environment (i.e., the surfaces of the tissue 242) surrounding the exterior of the stem 174.

Referring to FIG. 6b, the unitary body 162 of the applicator 160 is formed in six integrally joined sections, namely the proximal section 210, the flange section 212, the passage section 214, the slot section 216, the solid section 218, and the dome section 220.

The proximal coupler 170 is located in the proximal section 210, and the flange 172 is located in the flange section 212. A proximal portion of the stem 174 is located in the passage section 214, and the remainder of the stem is located in the slot section 216. The solid spacer 180 is located in the solid section 218, and the dome 182 is located in the dome section 220.

As noted above, the slot delivery passage 200, which is located in the slot section 216, is formed with a prescribed internal diameter. A proximal portion of an axial entry passage 222 is formed in the proximal coupler 170, and has a proximal entry opening 224 which is coincidental with the proximal end 166 of the body 162. A distal portion of the axial entry passage 222 is formed axially, and terminates, in the flange 172. Internal threads 226 are formed in the axial entry passage 222, which has an internal diameter greater than the prescribed internal diameter of the slot delivery passage 200.

An axial intermediate passage 228 is formed partially in the flange 172 and partially in the stem 174, and extends distally from a proximal end of the passage, located in the flange, to a distal end of the passage, located in the stem 174. The axial intermediate passage 228 is formed with an internal diameter, which is significantly less than the prescribed internal diameter of the slot delivery passage 200, and is considerably less than the internal diameter of the axial entry passage 222. An axial, funnel-shaped, transition passage 230 is axially interposed between the distal end of the axial entry passage 222 and the proximal end of the axial intermediate passage 228.

The axial entry passage 222, the axial transition passage 230, the axial intermediate passage 228, the slot delivery passage 200, and the slots 176 and 178 are all in communication, so that the cream 280 entering the proximal entry opening 224, under external force, will eventually exit, through outboard portions of the slots, to the environment externally of the body 162.

In the second applicator 160, the axial length of the slot delivery passage 200 (26 mm) is approximately two and one-half times the axial length of the axial intermediate passage 228 (10.65 mm). In addition, the diameter of the slot delivery passage 200 (3.18 mm) is approximately two and three-fifths times the diameter of the axial intermediate passage (1.22 mm). With the length and diameter of the slot delivery passage 200 as noted above, a sizable chamber 240 is formed by the slot delivery passage for the reception of significant amounts of the cream 280 within the chamber during use of the second applicator 160, for ultimate application of the cream 280 onto surfaces of the tissue 242 (FIG. 12) of a body opening 244 (FIG. 12) of the patient.

When the second applicator 160 is attached to, and used with, a rapid-delivery supply container, such as, for example, the piston-operable syringe 40 (FIG. 1), the cream 280 exits the syringe at a comparatively high-flow rapid-delivery rate. If the second applicator 160 had been formed with an axial intermediate passage, such as passage 228a (FIGS. 18 and 19), having the same prescribed internal diameter as the slot delivery passage 200, the cream 280 would be fed directly into the slot delivery passage at the above-noted high-flow rate.

In this instance, the cream 280, travelling at the high-flow rate, would tend to exit proximal portions of the slots 176 and 178 before the chamber 240 can be substantially filled with the cream. This action would result, undesirably, in large amounts of the cream 280 being dispensed onto the surfaces of tissue 242 of the body opening 244 adjacent proximal portions of the slots 176 and 178, and smaller amounts deposited onto the surfaces of the tissue adjacent distal portions of the slots.

This disparity of application of the cream 280 onto the surfaces of adjacent tissue 242 is alleviated by forming the axial intermediate passage 228 with the above-noted relatively smaller diameter and relatively shorter length, which is considerably less than the diameter and length of the slot delivery passage 200.

Figure 20:
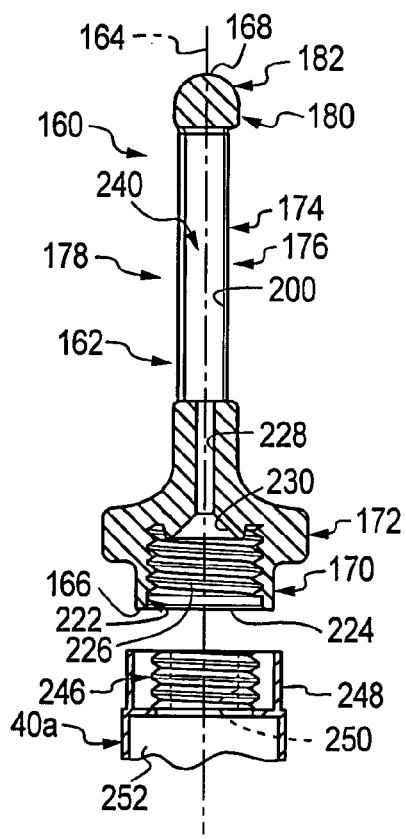
FIG. 20 is a sectional view showing an internally threaded proximal section of an applicator, which can form a respective threaded proximal section of each of the above-noted second through the fifth applicators, for assembly with an externally threaded hub of a syringe (partially shown) containing the medicinal cream, in accordance with certain principles of the invention.

In particular, and referring to FIGS. 6b and 20, a rapid-delivery cream-supply container, such as, for example, a piston-operable syringe 40a is formed with an externally threaded nipple 246 at a distal end 248 of the syringe, which is threadedly attachable to the internal threads 226 of the axial entry passage 222 of the second applicator 160. The nipple 246 is formed with an axial dispensing passage 250, which is in communication with a barrel 252 of the syringe 40a at a proximal end of the passage, and with the proximal end of the transition passage 230 of the second applicator 160.

After the syringe 40a is threadedly assembled with the applicator 160, as described above, the syringe 40a may be operated by use of a conventional, rapid-delivery stem and plunger arrangement (such as shown, for example, in FIG. 26) to urge the cream 280, at a rapid rate, from within the barrel 252 and into the dispensing passage 250. As the cream 280 exits the nipple 246, it encounters opposition to continued flow thereof at the proximal end of the axial intermediate passage 228, due to the significantly smaller diameter and length thereof. The flow of the cream 280 is thereby significantly limited to a much lower rate as the cream works its way through the smaller axial intermediate passage 228. The cream 280 then enters the proximal end of the slot delivery passage 200 at a rate that facilitates the filling of the chamber 240 before significant amounts of the cream exit through the slots 176 and 178.

Although limited amounts of the cream 280 exit through proximal portions of the slots 176 and 178 before the chamber 240 is filled, the above-noted parametrical relationships amongst the diameters and lengths of the axial intermediate passage 228 and the slot delivery passage 200 enhance the ability of the second applicator 160 to allow the chamber 240 to fill with the cream before significant amounts of the cream exit through the slots 176 and 178. This provides for a relatively even distribution of the cream 280 along the axial length "L" of the slots 176 and 178 after the chamber 240 is essentially filled with the cream.

In the preferred embodiment of the applicator 160, the solid spacer 180 and the dome 182 are solid as noted above. However, as shown in FIG. 6b, a distal passage 253 could be formed axially through the solid spacer 180 and the dome 182 from and through a distal end of the slot delivery passage 200 to and through the distal end 168, without departing from the spirit and scope of the invention.

Figure 18:
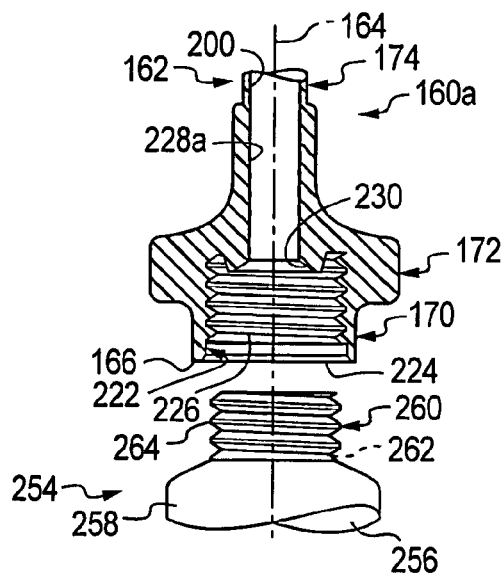
FIG. 18 is a sectional view showing an internally threaded proximal section of an applicator, which can form a respective threaded proximal section of each of the above-noted second through the fifth applicators, for assembly with an externally threaded end of a squeeze tube (partially shown) containing the medicinal cream, in accordance with certain principles of the invention.

Referring to FIG. 18, the structure of the second applicator 160 is modified, to provide a first modified applicator 160a, by increasing the diameter of the axial intermediate passage 228a to equal the diameter of the slot delivery passage 200. The first modified applicator 160a can be used with a slow-delivery, cream-supply container, such as, for example, a squeeze tube 254 of the type typically used to store toothpaste, which facilitates the dispensing of the toothpaste by squeezing the tube, typically by hand.

The squeeze tube 254 includes an enclosure 256 formed by a flexible wall 258 with a single-outlet nipple 260 having an axial outlet passage 262 formed therethrough, which communicates with the enclosure. The exterior of the nipple 260 is formed with threads 264 for receipt of a cap (not shown) with interior threads to seal the cream 280 within the squeeze tube 254.

With the cap removed, the exterior threads 264 of the nipple 260 can be assembled with the interior threads 226 of the first modified applicator 160a, whereby the axial intermediate passage 228a and the slot delivery passage 200, which are formed with the same diameter, are in communication with the enclosure 256.

The cream 280 within the tube 254 can then be forced from the enclosure 256 by squeezing the tube, typically by hand, to urge the cream through the outlet passage 262 and into the axial intermediate passage 228a, the slot delivery passage 200, and eventually through the slots 176 and 178 to the exterior of the first modified applicator 160a. Since the hand-squeezing force is typically low level, the small-diameter axial intermediate passage 228 of the applicator 160 is not required, and the cream 280 can be moved directly into the large-diameter axial intermediate passage 228a without undue exertion in the squeezing action.

Figure 19:
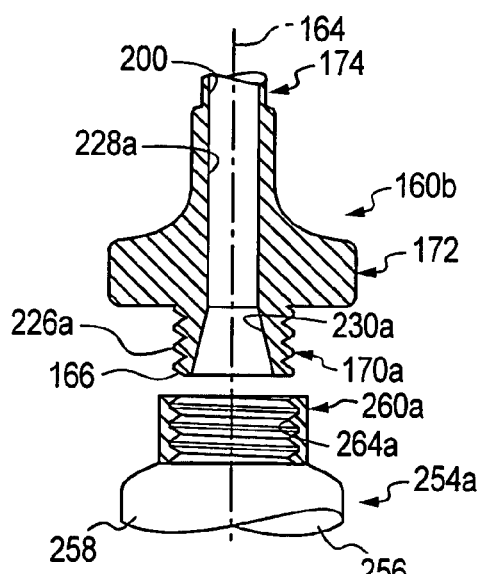
FIG. 19 is a sectional view showing an externally threaded proximal section of an applicator, which can form a respective threaded proximal section of each of the above-noted second through the fifth applicators, for assembly with an internally threaded end of a squeeze tube (partially shown) containing the medicinal cream, in accordance with certain principles of the invention.

Referring to FIG. 19, the structure of the second applicator 160 has been modified to form a second modified applicator 160b, where a proximal coupler 170a is formed with external threads 226a, and an axially-extended transition surface 230a, which extends proximally to the proximal end 166 of the applicator. A squeeze tube 254*a* is formed with internal threads 264*a*. The external threads 226*a* of the second modified applicator 160*b* can be assembled with internal threads 264*a* of the nipple 260*a* of a squeeze tube 254*a*. The tube 254*a* can be squeezed to force the cream 280 through the nipple 260*a*, the transition surface 230*a*, the slot delivery passage 200, and through the slots 176 and 178, in the manner noted above.

Figure 21:
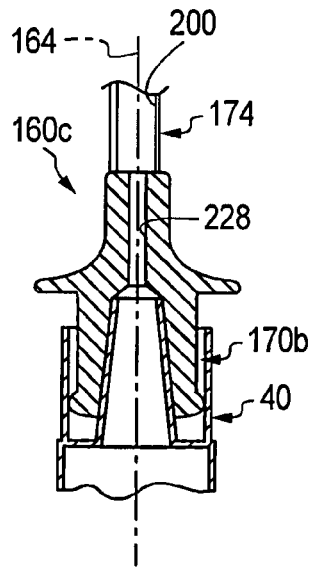
FIG. 21 is a sectional view showing a non-threaded proximal section of an applicator, such as the above-noted first applicator, for assembly with mating structure at the distal end of a syringe (partially shown) containing the medicinal cream, in accordance with certain principles of the invention.

Referring to FIG. 21, the structure of the second applicator 160 has been modified to form a third modified applicator 160*c* having a proximal coupler 170*b*, which is in assembly with the syringe 40 (FIG. 3), i.e., the rapid-delivery, cream-supply container, by use of the LUER LOK coupling arrangement noted above. The proximal coupler 170*b* is structurally similar to the proximal coupler 69 (FIG. 3) of the first applicator 66. The third modified applicator 160*c* operates in a manner similar to the operation of the assembled second applicator 160 and syringe 40*a*, as described above with respect to FIG. 20.

As shown partially at the bottom of FIG. 6*a*, and fully in FIG. 12, when the stem 174 of the applicator 160 is inserted into the body opening 244, surfaces of the tissue 242 are located at the radially outboard side of the slot 176. A similar condition occurs at the radially outboard side of the slot 178, as shown in FIG. 12. If the surfaces of the tissue 242 at the radially outboard sides of the slots 176 and/or 178 are dense, and/or the body opening 244 is small compared to the diameter of the stem 174, significant opposition to the outflow of the cream 280 onto the surfaces may result. This opposition results in an insufficient amount of the cream 280 being applied to surfaces of the tissue 242, which are adjacent the radially outboard sides of the slots 176 and 178.

Most of the structure of the below-described third, fourth, and fifth embodiments of an applicator, i.e., a third applicator 270, a fourth applicator 272, and a fifth applicator 274, respectively, is similar to corresponding structure of the above-described second applicator 160. Therefore, for consistency, the numeric, and the alpha-numeric, indicators for the structural features of the second applicator 160, which are common to corresponding structural features of each of the third, fourth, and fifth applicators 270, 272 and 274, respectively, will be used to identify the corresponding structural features of the third, fourth, and fifth applicators.

Referring to FIGS. 7 through 11, the third applicator 270 is formed with an extended flat surface 276, and an abbreviated side wall 176*h* spaced from, and generally parallel with, the extended side wall 176*b*, which is described above as the second extended side wall 176*b*, with respect to the second applicator 160.

In the description below, with respect to FIG. 11, and regarding the third applicator 270, the fourth applicator 272, and the fifth applicator 274, the extended side walls 176*b* and 178*a*, are the only side walls having the width "W." Therefore, with respect to slot 176 of each of the first, second, and third applicators 270, 272, and 274, respectively, reference to the only extended side wall associated with the slot 176 will be identified as "the extended side wall 176*b*," and, with respect to slot 178 of each of the first, second, and third applicators 270, 272, and 274, respectively, reference to the only extended side wall associated with the slot 178 will be identified as "the extended side wall 178*a*."

As further shown in FIG. 11, the abbreviated side wall 176*h* is located in the plane of the extended side wall 176*a* of the second applicator 160. Further, the abbreviated side wall 176*h* is formed with an inboard end at the integral juncture 340 with the slot delivery passage 200, and an outboard end at a juncture 341 with an inboard end of the extended flat surface 276. The abbreviated side wall 176*h* and the extended flat surface 276 are located on one side of the slot 176, and are spaced from the extended side wall 176*b*, which is located on the side of the slot opposite the one side.

The width of the abbreviated side wall 176*h* is less than the width "W," and is spaced inboard from the common external surface 195. The extended flat surface 276 is contiguous angularly with the abbreviated side wall 176*h* at the juncture 341 of the extended flat surface and the outboard end of the abbreviated side wall. The abbreviated side wall 176*h* extends from the inboard end thereof, at the juncture 340, outward to the juncture 341, from which the extended flat surface 276 extends to a juncture 342*b* with the common external surface 195.

The extended flat surface 276 extends angularly outward from the juncture 341 to the juncture 342*b* with the common external surface 195 at a flat-surface angle with respect to the abbreviated side wall 176*h*. The extended flat surface 276 also extends away from, and in an angularly direction with respect to, the extended side wall 176*b*, which, by virtue of the location of the slot 176, is spaced from the extended flat surface. Also, the extended flat surface 276 extends axially along the full axial length "L" of the slot 176

Referring to FIG. 11, without departing from the spirit and scope of the invention, in an alternate design of the applicator 270, an inboard end of an extended flat surface 276*c* (shown in dashed line) is located at the juncture 340 thereof with the slot delivery passage 200, which, as noted above, is the second side of the mouth of the slot, instead of being located at the outboard end of the abbreviated side wall 176*h*. In this alternate design, the extended flat surface 276*c* extends outward from the juncture 340 toward, and to, a juncture 342*m* at the common external surface 195. In this alternate design, the third applicator 270 will not include the abbreviated side wall 176*h* (FIG. 11), or any side wall in place thereof.

In similar fashion, without departing from the spirit and scope of the invention, in the alternate design of the applicator 270 as noted above, an inboard end of an extended flat surface 278*c* is located at the juncture 346*a* thereof with the slot delivery passage 200, instead of being located at the outboard end of the abbreviated side wall 178*h*. In this alternate design, the extended flat surface 278*c* extends outward from the juncture 346*a* toward, and to, a juncture 348*b* at the common external surface 195. In this instance, the third applicator 270 will not include the abbreviated side wall 178*h* (FIG. 11), or any side wall in place thereof.

Figure 10:
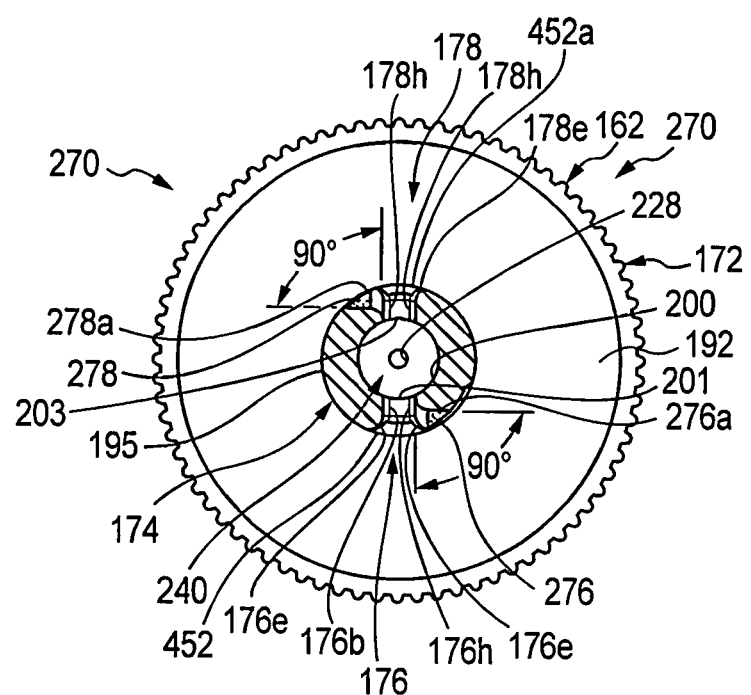
FIG. 10 is a partially-sectioned view taken along line 10-10 of FIG. 8 showing the angular relationship of the opposed side walls of each of the two slots and the respective flat surfaces, in accordance with certain principles of the invention.

In the illustration of FIGS. 10 and 11, the side walls 176*h* and 178*h* are each considerably less in width than the width "W" (FIG. 6*a*) as noted above, but could be greater than the width illustrated in FIGS. 10 and 11, and still be less than the width "W," without departing from the spirit and scope of the invention. As further shown in FIG. 10, the flat-surface angle for the extended flat surface 276, with respect to the extended side wall 176*b*, and with respect to the abbreviated side wall 176*h*, is ninety degrees, but could be at angles less or greater than ninety degrees without departing from the spirit and scope of the invention. In one representative example of a different flat-surface angle, as shown in FIG. 11, the flat-surface angle of the extended flat surface 276 is one hundred and thirty-five degrees.

Referring to FIG. 11, with the formation of the extended flat surface 276, at any flat-surface angle, a space 176*j* is formed, which is adjacent, and extends outward from, the extended flat surface to the common external surface 195, and which is laterally adjacent, and in communication with, the space 176*c* (FIGS. 6*a* and 11). The spaces 176*c* and 176*j* combine to form an extended slot 176*k*, which facilitates the flow of considerably more cream 280 to a much wider area of the surfaces of the tissue 242 than is available with the flow of the cream through the space 176c only, of the second applicator 160 (FIG. 6a).

Referring to FIG. 11, within the extended slot 176k, and with the formation of the extended flat surface 276, a proximal wall 176m is formed, and is located in a common plane with the proximal wall 176d. The proximal wall 176m is contiguous with, and, preferably, is perpendicular to, the extended flat surface 276, but could be at angles other than perpendicular without departing from the spirit and scope of the invention. In effect, the proximal wall 176m is a continuation of the proximal wall 176d, which, together, form an extended proximal wall 176p.

In addition, a proximal transition surface 176n extends in a proximal direction between a distal juncture 450m and a proximal juncture 452m. Further, the proximal transition surface 176n is a continuation of the proximal transition surface 176e, which, together, form an extended proximal transition surface 176q.

Figure 7:
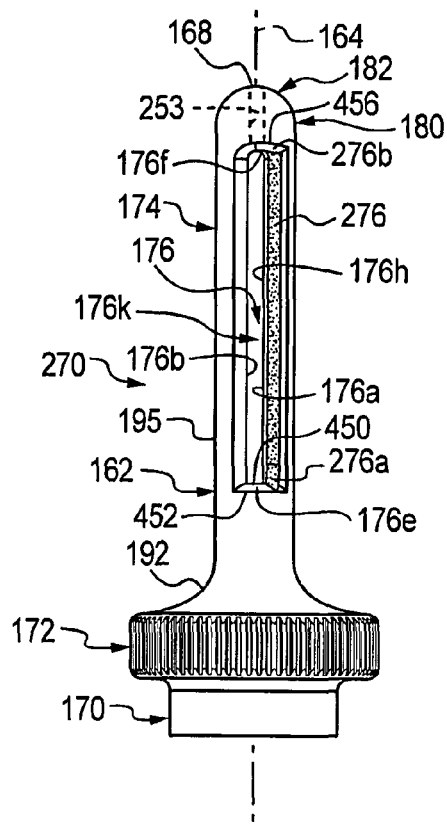
FIG. 7 is a front view of a third embodiment of an applicator ("third applicator") showing one of two axially-elongated, diametrically-opposed slots, with each slot formed with two opposed, spaced, side walls and a flat, or angular, surface contiguous with one of the side walls, where a flat surface extends axially from a proximal end to a distal end of the slot to facilitate the application of a medicinal cream through the full axial length of the slot, over the flat surface, and onto tissue of body openings of a patient, in accordance with certain principles of the invention.
Figure 8:
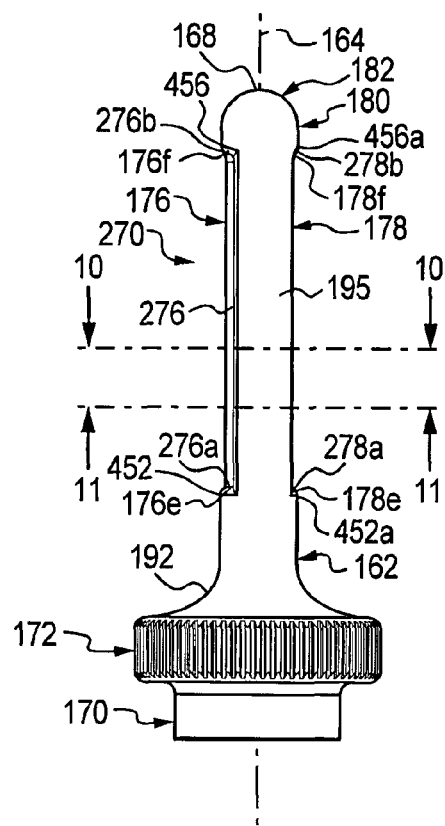
FIG. 8 is a side view showing additional features of the third applicator of FIG. 7, in accordance with certain principles of the invention.
Figure 9:
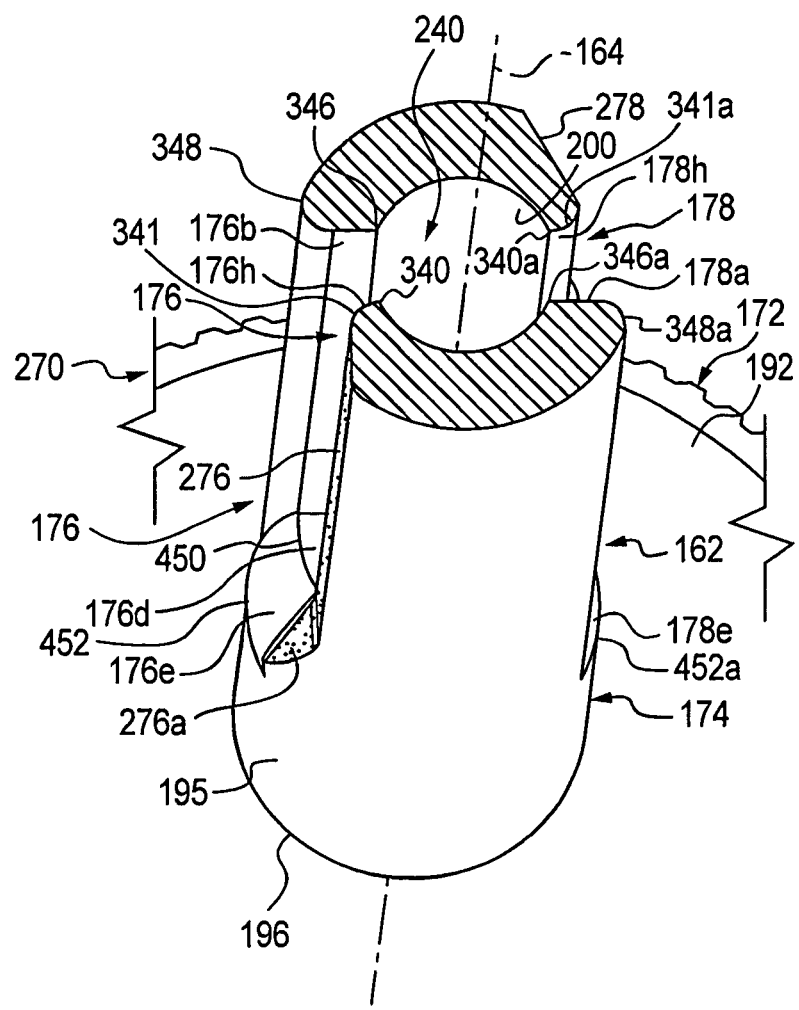
FIG. 9 is a partially-sectioned, perspective view showing a portion of the third applicator of FIG. 7 with a slot section, or stem, of the body thereof being sectioned to show interior structure of the two slots in relation to the respective flat surfaces, in accordance with certain principles of the invention.

As shown in FIGS. 7 and 9, a triangularly-shaped, proximal, flat transition surface 276a extends in a proximal direction and outward to the common external surface 195 from a proximal end of the extended flat surface 276, and is located adjacent the proximal transition surface 176e. A similar triangularly-shaped, distal, flat, transition surface 276b (FIG. 7) extends in a distal direction and outward to the common external surface 195 from a distal end of the extended flat surface 276, and is located adjacent the distal transition surface 176f (FIG. 8). The proximal and distal flat transition surfaces 276a and 276b, respectively, form proximal and distal portions, respectively, of, and are thereby included in, the extended flat surface 276.

Referring again to FIGS. 7 through 11, the third applicator 270 is formed with an extended flat surface 278, and an abbreviated side wall 178h spaced from, and generally parallel with, the extended side wall 178b, which is the only extended side wall associated with the slot 178. As shown in FIG. 11, the abbreviated side wall 178h is formed with an inboard end at the integral juncture 346a with the slot delivery passage 200, and an outboard end at a juncture 341a with the extended flat surface 278. The inboard end of the extended flat surface 278 is located on one side of the slot 178, and is spaced from the extended side wall 178a, which is located on the opposite side of the slot.

The width of the abbreviated side wall 178h is less than the width "W," and is spaced inboard from the common surface 195. The extended flat surface 278 is contiguous angularly with the abbreviated side wall 178h at the juncture 341a of the extended flat surface and the outboard end of the abbreviated side wall. The abbreviated side wall 178h extends from the inboard end thereof, at the juncture 340a, outward to the juncture 341a, from which the extended flat surface 278 extends to a juncture 348a with the common surface 195.

The extended flat surface 278 extends angularly outward from the juncture 341a to the juncture 348a with the common external surface 195, at a flat-surface angle with respect to the abbreviated side wall 178h. The extended flat surface 278 also extends away from, and in an angularly direction with respect to, the extended side wall 178a, which, by virtue of the location of the slot 178, is spaced from the extended flat surface. Also, the extended flat surface 278 extends axially along the full axial length "L" of the slot 178.

It is noted that, without departing from the spirit and scope of the invention, an inboard end of an extended flat surface 278a (shown in dashed line) could be located at the juncture 346a thereof with the slot delivery passage 200, with the extended flat surface extending outward toward, and to, a juncture 348b at the common external surface 195. In this instance, the third applicator 270 will not include a side wall situated in the place of the side wall 178b (FIG. 6a), or any side wall extending outward from the juncture 340a.

In the illustration of FIG. 10, the side wall 178h is considerably less in width than the width "W" (FIG. 6a), but could be greater than the width illustrated in FIGS. 10 and 11, and still be less than the width "W," without departing from the spirit and scope of the invention. As further shown in FIG. 10, the flat-surface angle for the extended flat surface 278, with respect to the extended side wall 178a, is ninety degrees, but could be at angles less or greater than ninety degrees without departing from the spirit and scope of the invention. In one example, the flat-surface angle of the extended flat surface 278 could be one hundred and thirty-five degrees, such as shown in FIG. 11 with respect to the extended flat surface 276.

Referring to FIG. 11, with the formation of the extended flat surface 278, at any flat-surface angle, a space 178j is formed, which is adjacent, and extends outward from, the extended flat surface to the common external surface 195, and which is laterally adjacent, and in communication with, the space 178c (FIGS. 6a and 11). The spaces 178c and 178j combine to form an extended slot 178k, which facilitates the flow of considerably more cream 280 to a much wider area of the surfaces of the tissue 242 than is available with the flow of the cream through the space 178c only, of the second applicator 160 (FIG. 6a).

In similar fashion, within the extended slot 178k, and with the formation of the extended flat surface 278, a proximal wall 178m is formed, and is located in a common plane with the proximal wall 178d. The proximal wall 178m is contiguous with, and, preferably, is perpendicular to, the extended flat surface 278, but could be at angles other than perpendicular without departing from the spirit and scope of the invention. In effect, the proximal wall 178m is a continuation of the proximal wall 178d, which, together, form an extended proximal wall 178p.

In addition, a proximal transition surface 178n extends in a proximal direction between a distal juncture 450n and a proximal juncture 452n. Further, the proximal transition surface 178n is a continuation of the proximal transition surface 178e, which, together, form an extended proximal transition surface 178q.

As shown in FIGS. 7 and 9, a triangularly-shaped, proximal, flat transition surface 278a extends in a proximal direction and outward to the common external surface 195 from a proximal end of the extended flat surface 278, and is located adjacent the distal transition surface 178e. A similar triangularly-shaped, distal, flat transition surface (not shown) extends in a distal direction and outward to the common external surface 195 from a distal end of the extended flat surface 278, and is located adjacent the distal transition surface 178f (FIG. 8). The proximal and distal flat transition surfaces 278a and 278b, respectively, form portions of the extended flat surface 278.

In the manner described above, the extended flat surface 276, including the proximal and distal transition surfaces 276a and 276b (FIGS. 7 and 8), respectively, extends the axial length "L" of the slot 176, i.e., as noted above and shown in FIGS. 6b, 7 and 8, between (1) the proximal juncture 452 of the proximal transition surface 176e and (2) the distal juncture 456 of the distal transition surface 176f (FIG. 6b), with the common external surface 195.

Similarly, as described above, the extended flat surface 278, including the transition surface 278a and the transition surface 178g (FIG. 6b) at the distal end of the slot, extends the axial length "L" of the slot 178, i.e., as noted above, between (1) the proximal juncture 452*a* of the proximal transition surface 178*e* with the common external surface 195 and (2) the distal juncture 456*a* of the distal transition surface 178*g* with the common surface.

In similar fashion, with the formation of the extended flat surface 278, a proximal wall 178*m* is formed, and is located in a common plane with the proximal wall 178*d*. The proximal wall 178*m* is contiguous with, and, preferably, is perpendicular to, the extended flat surface 278, but could be at angles other than perpendicular without departing from the spirit and scope of the invention. In effect, the proximal wall 178*m* is a continuation of the proximal wall 178*d*, which, together, form an extended proximal wall 178*p*.

In addition, a proximal transition surface 178*n* extends in a proximal direction between a distal juncture 450*n* and a proximal juncture 452*n*. Further, the proximal transition surface 178*n* is a continuation of the proximal transition surface 178*e*, which, together, form an extended proximal transition surface 178*q*.

Referring further to FIG. 11, the straight-line proximal juncture 450 and the curve-line proximal juncture 450*m* are joined to form an extended proximal juncture 451. In particular, with respect to the slot 176, the proximal juncture 450*m* extends perpendicularly from the extended side wall 176*b* toward the common external surface 195. The proximal juncture 450*m* is a continuation of the proximal juncture 450, which extends to the juncture 342*b* with the common external surface 195.

With respect to the slot 178, the straight-line proximal juncture 450*a* and a curve-line proximal juncture 450*n* are joined to form an extended proximal juncture 451*a*. In particular, with respect to the slot 178, the proximal juncture 450*a* extends perpendicularly from the extended side wall 178*a* toward the common external surface 195. The proximal juncture 450*n* is a continuation of the proximal juncture 450*a*, and extends to the juncture 348*a* with the common external surface 195.

The extended proximal junctures 451 and 451*a* represent the preferred embodiment of a combined proximal juncture. Other extended proximal junctures could be formed without departing from the spirit and scope of the invention, such as, for example, extended proximal junctures 451*b* and 451*c*, 451*d* and 451*e*, and 451*f* and 451*g*, described below and illustrated in FIGS. 11*a*, 11*b*, and 11*c*, respectively.

Figure 11A:
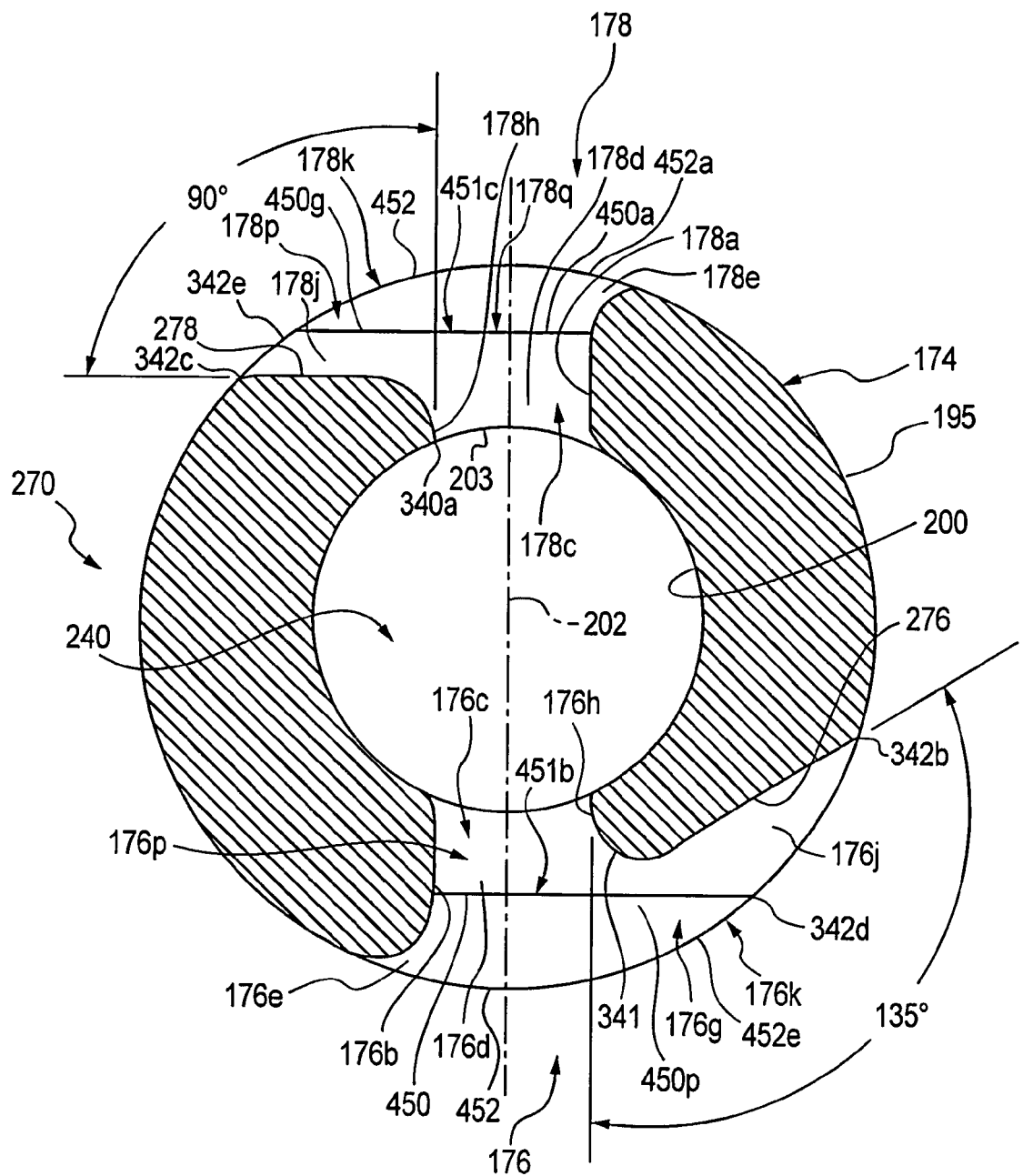
FIGS. 11a, 11b, and 11c are enlarged views of the sectioned portion of the slot section of FIG. 10 showing third, fourth, and fifth embodiments, respectively, of the juncture of FIG. 6a, in accordance with certain principles of the invention.

Referring to FIG. 11*a*, the straight-line proximal juncture 450 and a straight-line proximal juncture 450*p* are joined to form the extended proximal juncture 451*b*. In particular, with respect to the slot 176, the proximal juncture 450 extends perpendicularly from the extended side wall 176*b* toward the common external surface 195. The proximal juncture 450*p* is a continuation of the proximal juncture 450, which extends to a juncture 342*d* with the common external surface 195.

With respect to the slot 178, the straight-line proximal juncture 450*a* and a straight-line proximal juncture 450*q* are joined to form the extended proximal juncture 451*c*. In particular, with respect to the slot 178, the proximal juncture 450*a* extends perpendicularly from the extended side wall 178*a* toward the common external surface 195. The proximal juncture 450*q* is a continuation of the proximal juncture 450*a*, and extends to a juncture 342*e* with the common external surface 195.

The combined proximal walls 176*p* and 178*p*, and the combined proximal transitional surfaces 176*q* and 178*q*, as shown in FIG. 11, also appear in FIG. 11*a*, except that illustrations of the walls and surfaces shown in FIG. 11*a* are altered from the showing in FIG. 11 due to the different configurations of the extended proximal junctures 451,451*a* (FIG. 11) and the extended proximal junctures 451*b*,451*c* (FIG. 11*a*).

Figure 11B:
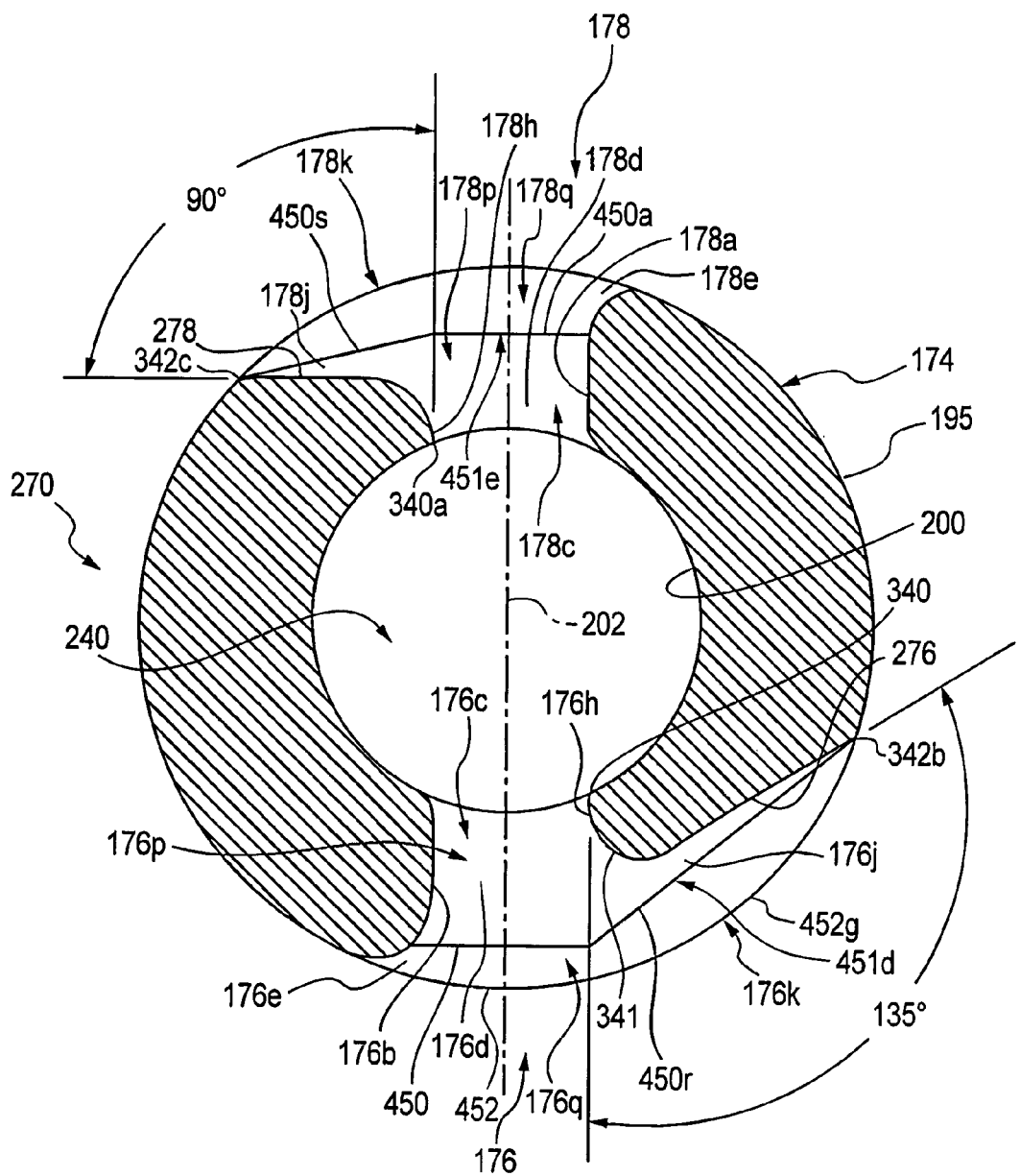

Referring to FIG. 11*b*, the straight-line proximal juncture 450 and a straight-line proximal juncture 450*r* are joined to form an extended proximal juncture 451*d*. In particular, with respect to the slot 176, the proximal juncture 450 extends perpendicularly from the extended side wall 176*b* toward the common external surface 195. The proximal juncture 450*r* is a continuation of the proximal juncture 450, which extends to the juncture 342*b* with the common external surface 195.

With respect to the slot 178, the straight-line proximal juncture 450*a* and a straight-line proximal juncture 450*s* are joined to form an extended proximal juncture 451*e*. In particular, with respect to the slot 178, the proximal juncture 450*a* extends perpendicularly from the extended side wall 178*a* toward the common external surface 195. The proximal juncture 450*s* is a continuation of the proximal juncture 450*a*, and extends to the juncture 342*c* with the common external surface 195.

The combined proximal walls 176*p* and 178*p*, and the combined proximal transitional surfaces 176*q* and 178*q*, as shown in FIG. 11, also appear in FIG. 11*b*, except that illustrations of the walls and surfaces shown in FIG. 11*b* are altered from the illustration in FIG. 11 due to the different configurations of the extended proximal junctures 451,451*a* (FIG. 11) and the extended proximal junctures 451*d*,451*e* (FIG. 11*b*).

Figure 11C:
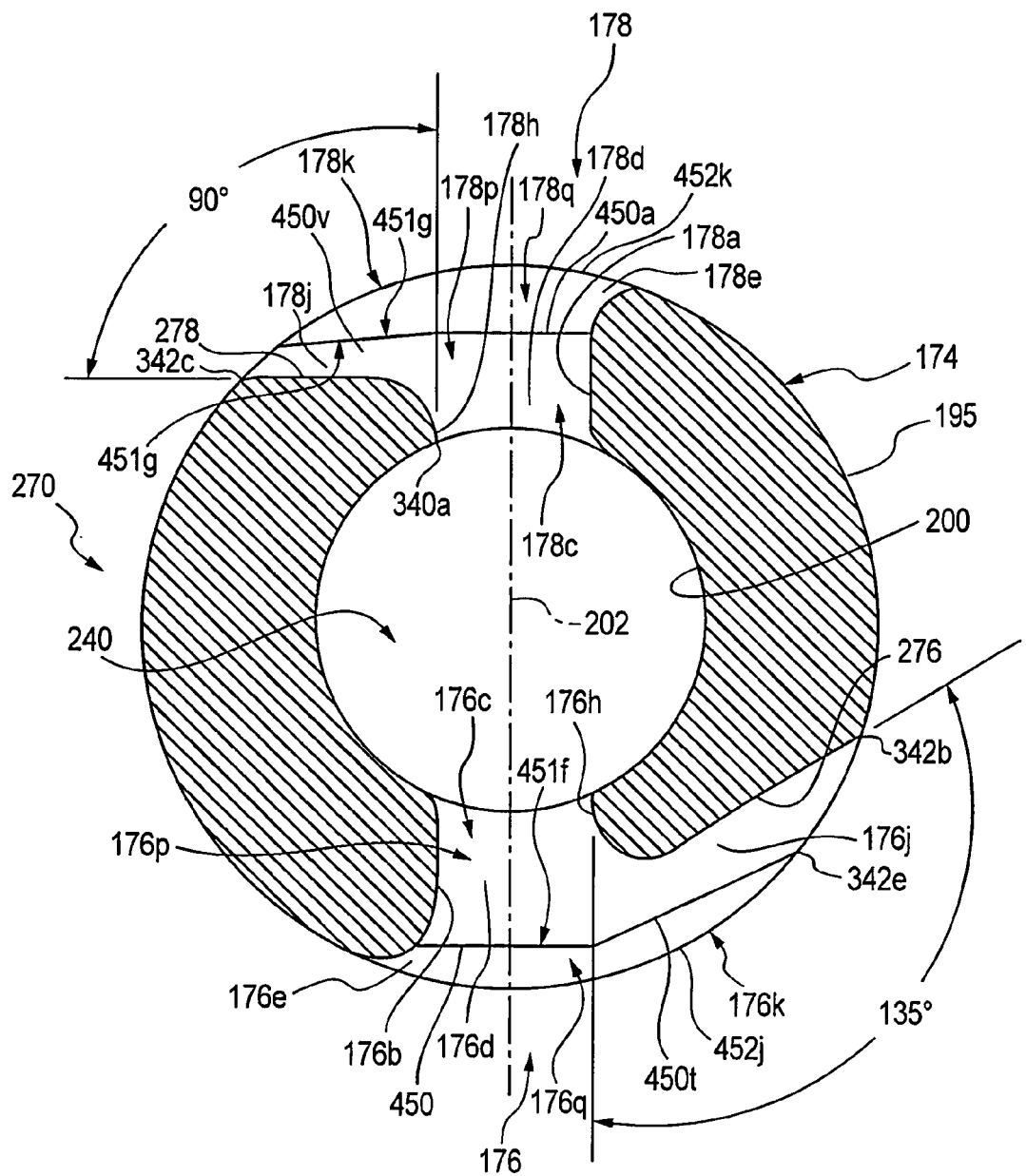

Referring to FIG. 11*c*, the straight-line proximal juncture 450, and a straight-line proximal juncture 450*t* are joined to form an extended proximal juncture 451*f*. In particular, with respect to the slot 176, the proximal juncture 450 extends perpendicularly from the extended side wall 176*b* toward the common external surface 195. The proximal juncture 450*t* is a continuation of the proximal juncture 450, which extends to a juncture 342*e* with the common external surface 195.

With respect to the slot 178, the straight-line proximal juncture 450*a* and a straight-line proximal juncture 450*v* are joined to form an extended proximal juncture 451*g*. In particular, with respect to the slot 178, the proximal juncture 450*a* extends perpendicularly from the extended side wall 178*a* toward the common external surface 195. The proximal juncture 450*v* is a continuation of the proximal juncture 450*a*, and extends to the juncture 342*c* with the common external surface 195, The combined proximal walls 176*p* and 178*p*, and the combined proximal transitional surfaces 176*q* and 178*q*, as shown in FIG. 11, also appear in FIG. 11*c*, except that configurations of the walls and surfaces shown in FIG. 11*c* are altered from the showing in FIG. 11 due to the different configurations of the extended proximal junctures 451,451*a* (FIG. 11) and the extended proximal junctures 451*f*,451*g* (FIG. 11*c*).

As shown in FIG. 12, the stem 174 of the third applicator 270 is located within the body opening 244 of the patient, with the illustration looking outward from within the opening. The cream 280 enters the chamber 240 as supplied from the cream-supply containers 40, 40*a* or 254 as described herein. The cream 280 then passes through the slots 176 and 178, and is applied to exposed surfaces of the tissue 242 adjacent the outboard ends of the slots.

As indicated by a flow-direction arrow 282, shown within the slot 176, some portions of the flowing cream 280 follow a path generally parallel to the side walls 176*b* and 176*h*, resulting in an application of the cream onto the surfaces of the tissue 242 in the direct path of the flowing cream. With the formation of the flat surface 276, the side wall 176*h* is shorter in comparison to the side wall 176b resulting in a wider opening of the slot 176 adjacent the flat surface. With the wider opening of the slot 176, some of the cream 280 follows a path defined by flow-direction arrows 282a and 282b, resulting in a generally angular application of the cream to additionally exposed surfaces of the tissue 242, which are now exposed due to the formation of the flat surface 276. Other portions of the cream 280 will be applied directly onto the additionally exposed surfaces, in addition to the angular application thereon.

In similar fashion, as indicated by a flow-direction arrow 284, shown within the slot 178, some portions of the flowing cream 280 follow a path generally parallel to the side walls 178a and 178h, resulting in a direct application of the cream onto the surfaces of the tissue 242. With the formation of the flat surface 278, the side wall 178b is shorter in comparison to the side wall 178a resulting in a wider opening of the slot 178 adjacent the flat surface. With the wider opening of the slot 178, some of the cream 280 follows a path defined by flow-direction arrows 284a and 284b, resulting in a generally angular application of the cream to additionally exposed surfaces of the tissue 242, which are now exposed due to the formation of the flat surface 278. Other portions of the cream 280 will be applied directly onto the additionally exposed surfaces, in addition to the angular application thereon.

By forming the extended flat surfaces 276 and 278 on the third applicator 270 as described above, a desirable abundance of the cream 280 is applied to two relatively wide, and axially long, areas of the surfaces of the tissue 242, particularly compared to areas of the surface to which the cream 280 is applied by use of the second applicator 160.

Referring to FIG. 11, as described above with respect to the alternate design, the flat surface 276a extends, at a selected flat-surface angle, from the juncture 340 directly to a juncture 342m with the common external surface 195, wherein the abbreviated side wall 176h, or any side wall in place thereof, will not be formed in such alternate design. In similar fashion, in the alternate design, a flat surface 278m extends, at a selected flat-surface angle, from the juncture 340a directly to a juncture 342n with the common external surface 195, wherein the abbreviated side wall 178h, or any side wall in place thereof, will not be formed in such alternate design.

With the selection of appropriate flat-surface angles for the flat surfaces 276m and/or 278m, the slots 176 and 178 are widened even farther to facilitate the application of the cream 280 onto additional surfaces of the tissue 242, when compared to surfaces of the tissue, which are accessible when using the flat surfaces 276 and/or 278.

Figure 13:
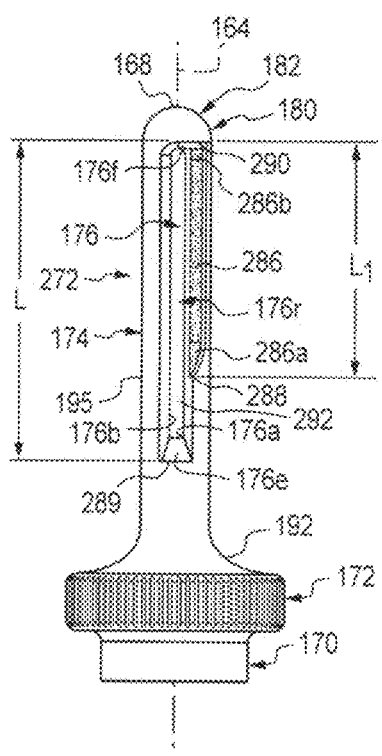
FIG. 13 is a front view of a fourth embodiment of an applicator ("the fourth applicator") which is similar to the third applicator, as shown in FIG. 7, except that the flat surface of each slot extends along an axial portion of the respective slot, from a location intermediate the proximal end and the distal end of the slot, to the distal end of the slot, in accordance with certain principles of the invention.
Figure 14:
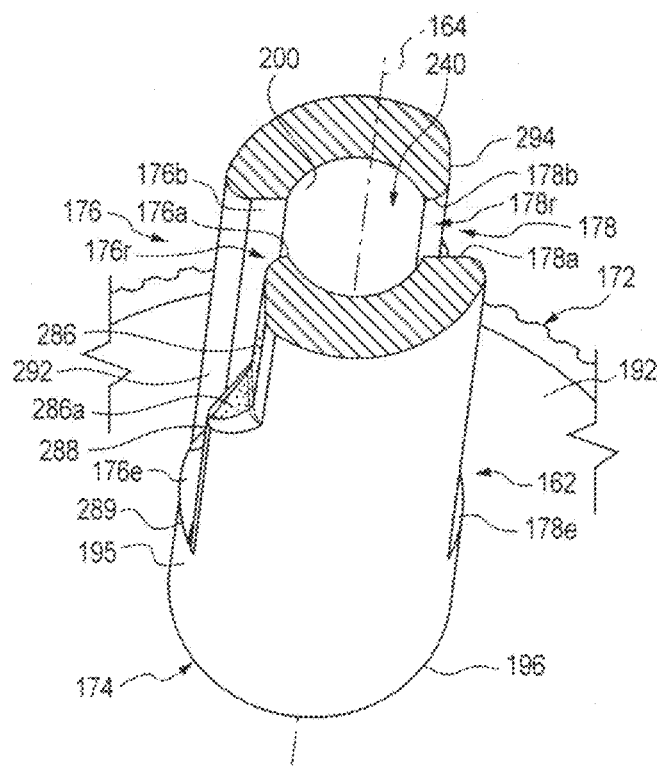
FIG. 14 is a partially-sectioned, perspective view showing a portion of the fourth applicator, in a manner similar to the third applicator of FIG. 8, with a slot section, or stem, of the body thereof being sectioned to show interior structure of the two slots in relation to the respective flat surfaces, in accordance with certain principles of the invention.

Referring to FIGS. 13 and 14, the fourth applicator 272 is similar to the third applicator 270 (FIG. 7) except that an abbreviated flat surface 286 of the fourth applicator is formed with an axial length "$L_1$" which is less than the axial length "L" of the extended flat surface 276 (FIG. 7) of the third applicator. A proximal end 288 of the abbreviated flat surface 286 is located at an intermediate point along the axial length of the slot 176, between a proximal end 289 and a distal end 290 of the slot, and extends axially to the distal end 290 of the slot. The abbreviated flat surface 286 includes a proximal transition surface 286a, and a distal transition surface 286b.

The portion of the slot 176 of the fourth applicator 272, which includes the abbreviated flat surface 286, is formed with an extended slot 176r by virtue of the presence of the abbreviated flat surface in the same manner as is provided by the extended slot 176k of the third applicator 270. This facilitates the flow of considerably more cream 280, through the extended slot 176r, to a much wider area of the surfaces of the tissue 242 adjacent the abbreviated flat surface 286 than is available with the flow of the cream through the space 176c only, of the second applicator 160 (FIG. 6a).

A proximal portion 292 of the slot 176 of the fourth applicator 272, which is located between the proximal end 289 of the slot and the intermediate point thereof, at the proximal end 288 of the proximal transition surface 286a structurally remains as illustrated in FIGS. 5 through 6b, i.e., each of the side walls 176a and 176b are formed with the width "W," (FIG. 6a) and the proximal portion of the slot is not formed with a flat surface.

In like fashion, as shown in FIG. 14, an abbreviated flat surface 294 of the slot 178, of the fourth applicator 272, is formed with the axial length "$L_1$" (FIG. 13) which is less than the axial length "L" of the extended flat surface 276 (FIG. 7) of the third applicator 270 as described above. A proximal end of the abbreviated flat surface 294 is located at an intermediate point along the axial length of the slot 178, between the proximal and distal ends of the slot, and extends axially to a distal end of the slot, all in the same manner as the slot 176 (FIG. 13) of the fourth applicator 272. The abbreviated flat surface 294 includes a proximal transition surface, and a distal transition surface. A proximal portion of the slot 178 of the fourth applicator 272, which is between the proximal end of the slot and the intermediate point thereof, structurally remains as illustrated in FIGS. 6, 6a, and 6b, i.e., each of the side walls 178a and 178b have the width "W," and the proximal portion of the slot does not include a flat surface.

After the stem 174 of the fourth applicator 272 has been inserted into the body opening 244 (FIG. 12) of the patient, the cream 280 is moved in a distal direction from the syringe 40 (FIG. 1), the syringe 40a (FIG. 20), or the squeeze tube 254 (FIG. 18), into the axial intermediate passage 228 (FIG. 20) or 228a (FIG. 18), respectively, of the fourth applicator, as described above. Eventually, the cream 280 flows into the slot delivery passage 200 to begin filling the chamber 240, from the proximal end to the distal end thereof. As the cream 280 is moved into proximal portions of the chamber 240, small amounts of the cream begin to be dispensed through the adjacent portions of the slots 176 and 178, which do not include a flat surface, in the manner described above with respect to the second applicator 160. However, the rate of flow of the cream 280 into the chamber 240 is greater than the rate of flow of the cream outward through the proximal portions of the slots 176 and 178, whereby major portions of the cream continue to move distally into the chamber.

Eventually, the cream 280 reaches the intermediate point of the slots 176 and 178, where the proximal ends of the abbreviated flat surfaces 286 and 294 of the slots are located. As the mass of cream 280 continues to move distally beyond the proximal ends of the abbreviated flat surfaces 286 and 294, significant amounts of the cream are fed through the extended slot 176r and a similarly located extended slot 178r, and over the abbreviated flat surfaces 286 and 294, respectively. After the chamber 240 is essentially filled with the cream 280, and the cream is continuing to be fed into the proximal end of the chamber 240, (1) relatively small amounts of the cream continue to be fed through the proximal non-flat-surface portions of the slots 176 and 178, as described above, and (2) greater amounts of the cream are fed through the portions of the extended slots 176r and 178r distally beyond the proximal ends of, and over, the abbreviated flat surfaces 286 and 294.

Thus, the structure of the fourth applicator 272, as described above, facilitates selective placement, with selective different amounts, of the cream 280 onto different portions of the surfaces of the tissue 242.

Each of the abbreviated flat surfaces 286 and 294 of the fourth applicator 272 could be placed at any of many locations along the axial length "L" of the slots 176 and 178, with a length, such as, for example, "L₁" which is less than the axial length "L" without departing from the spirit and scope of the invention. For example, the respective proximal ends of the abbreviated flat surfaces 286 and 294 could be located at the proximal ends of the slots 176 and 178, respectively, and the distal ends thereof located at the above-noted intermediate points (FIGS. 13 and 14) of the respective slots. In another example, two or more axially spaced sections of abbreviated flat surfaces 286 could be located along the slot 176, and two or more axially spaced abbreviated flat surfaces 294 could be located along the slot 178. Or, for example, the proximal ends of the abbreviated flat surfaces 286 and 294 could be spaced distally from the proximal ends of the slots 176 and 178, respectively, and the distal ends of the abbreviated flat surfaces could be spaced from the respective distal ends of the slots. Further, for example, the abbreviated flat surfaces 286 and 294 could be at different radial positions along the respective slots 176 and 178, and, therefore, not radially aligned. Additionally, for example, the abbreviated flat surfaces 286 and 294 could be formed at different flat-surface angles in the manner illustrated in FIG. 11.

Figure 15:
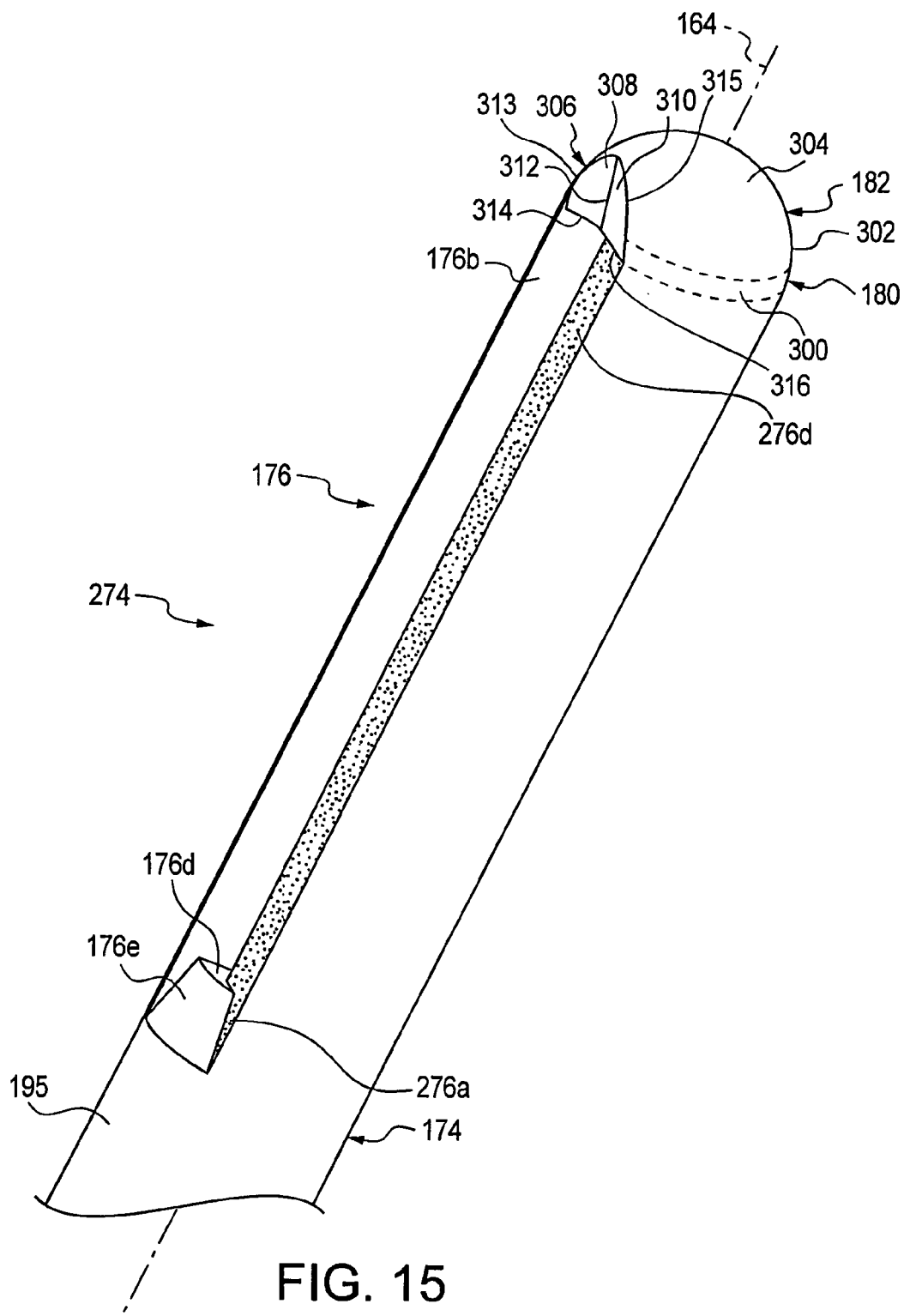
FIG. 15 is a perspective view showing a fifth embodiment of an applicator ("the fifth applicator") having a pair of opposing slots (one shown), with each slot formed with a flat surface and with a distal transition surface, or cleft, of the slot which extends over and into the outer surface of a solid section, and partially over and into the outer surface of a dome section, of the fifth applicator, in accordance with certain principles of the invention.
Figure 16:
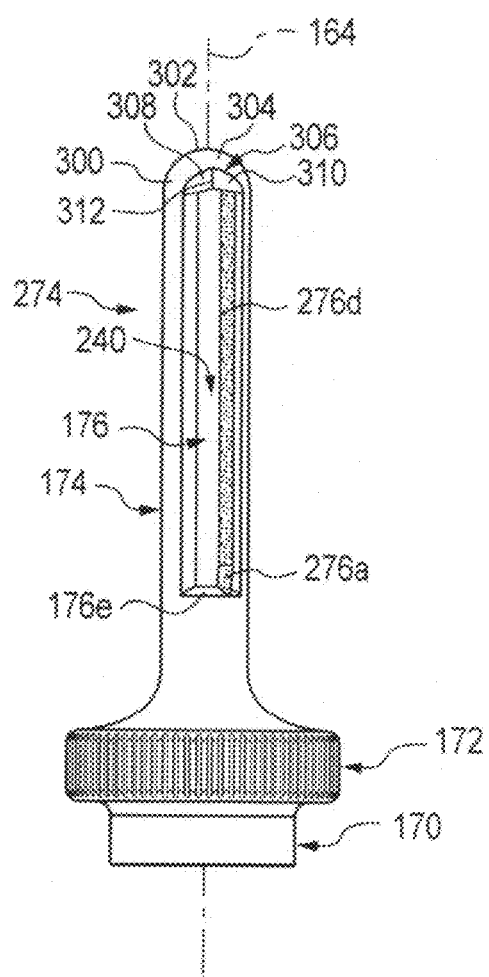
FIG. 16 is a front view of the fifth applicator showing a first slot, of the pair of slots, and further showing the flat surface, and the distal transition surface, of the first slot, in accordance with certain principles of the invention.
Figure 17:
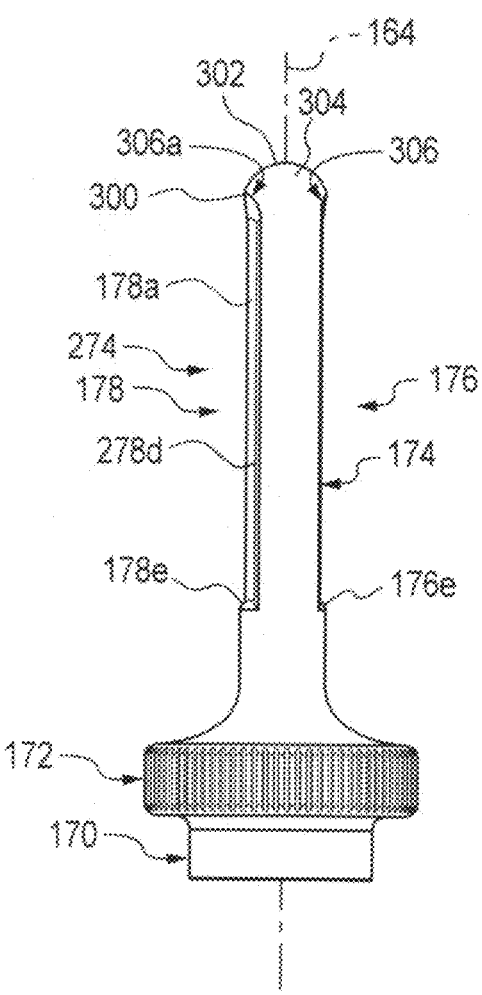
FIG. 17 is a side view of the fifth applicator showing a second slot, of the pair of slots, and further showing the flat surface, and the distal transition surface, of the second slot, in accordance with certain principles of the invention.

Referring to FIGS. 15, 16 and 17, the fifth applicator 274 is structurally, and functions in a manner, similar to the third applicator 270 (FIGS. 7, 8, and 9), except in external surface areas of the solid spacer 180 and the dome 182 distally beyond the distal end of extended flat surfaces 276d and 278d. The extended flat surfaces 276d and 278d are similar in structure and function to the extended flat surfaces 276 and 278, respectively, of the third applicator 270.

In the fifth applicator 274, the solid spacer 180 is formed with an external surface 300, and the dome 182 is formed with an external surface 304. The external surfaces 300 and 304 are a continuation of the common external surface 195 of the stem 174, and the solid spacer 180 and the dome 182 combine to form a solid portion of the stem.

A cleft 306, which is a continuation of, and a part of, the slot 176, is formed in adjacent contiguous portions of the surfaces 300 and 304 of the solid spacer 180 and the dome 182, respectively, which as noted above is a solid portion of the stem 174. The cleft 306 is formed with two generally triangular-shaped sections 308 and 310 having a common leg 312 of the two sections, with the common leg being joined along a common generally-axial juncture of the two sections. Each of the two triangular-shaped sections 308 and 310 of the cleft 306 is further formed with each of the base legs 314 and 316, respectively, having an inboard end which joins with, and at, a proximal end of the common leg 312.

Each of the two sections 308 and 310 of the cleft 306 is also formed with linking legs 313 and 315, respectively, with each linking leg having a proximal end joined with an outboard end of the base legs 314 and 316, respectively, and a distal end joined with, and at, a distal end of the common leg 312. The entirety of each of the linking leg 313 and 315 is formed at a juncture of each leg with the common external surface 195.

The generally-axial common leg 312 extends, and is angled outward from the proximal end thereof in a direction away from the axis 164, which is spaced therefrom, to a distal end of the common leg. Each of the base legs 314 and 316 are angled inward from an outboard end thereof, at a juncture with the external common surface 195, and extends along a proximal end of the cleft 306 to a common juncture of an inboard end thereof with a proximal end of the common leg 312. Each of the triangular sections 308 and 310 slopes inward from the linking legs 313 and 315, respectively, to the common leg 312, and from the base legs 314 and 316, respectively, to form a trough-like structure which guides the flow of the cream 280 outward from the cleft 306 to adjacent surfaces of the tissue 242.

The base legs 314 and 316 form the widest portion of the cleft 306 at the axially proximal end thereof, and the narrowest point at the axially distal end of the cleft. The proximal end of the cleft 306 is contiguous with and extends across the distal end of the slot 176 to provide for maximum continuous flow of the cream 280 from the slot to surfaces of the tissue 242 adjacent the cleft.

A cleft 306a (FIG. 17), which is structurally similar to the cleft 306, is formed distally of the slot 178 in the same manner described above with respect to the slot 176.

When the stem 174 is located within the body opening 244 of the patient, the clefts 306 and 306a are located adjacent surfaces of the tissue 242. Eventually, the cream 280 is moved into the chamber 240 (FIG. 16), and reaches the distal end thereof. As the cream 280 exits through the slots 176 and 178 (FIG. 17), distal portions of the cream will enter proximal portions of the clefts 306 and 306a and will be urged distally through the trough-like clefts to move the cream axially outward, thereby spreading the cream onto the surfaces of the tissue 242, which are adjacent the clefts. With the location of the clefts 306 and 306a, use of the fifth applicator 274 facilitates an extension of the cream 280 distally beyond the distal end of the slots 176 and 178.

It is noted that, even with the formation of the clefts 306 and 306a in exterior portions of the surfaces 300 and 304 of the solid section 180 and the dome 302, respectively, there are no openings through the solid section and the dome, both of which are solid.

In the illustration of FIG. 17, the fifth applicator 274 is positioned to show the slot 178, an extended side wall 178a, a proximal transition surface 178e, and an extended flat surface 278d, all of which are structurally, and function in the same manner as, the corresponding structure of the slot 176 (FIGS. 15 and 16).

In the preferred embodiments of the invention, the surfaces 276, 278, 286, 294, 276d, and 278d are flat, but could be other than flat, such as, for example, at least portions of the surfaces being formed with peaks, depressions, undulations, being concave or convex, and the like, without departing from the spirit and scope of the invention.

Figure 26:
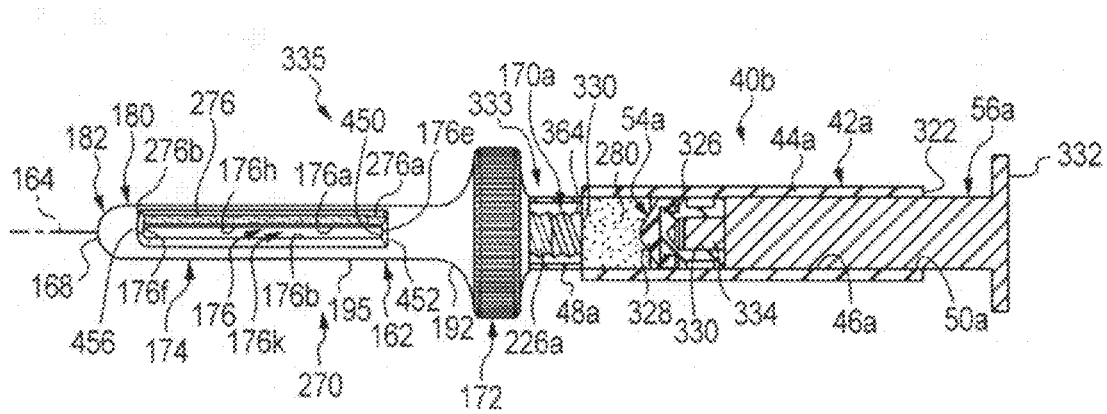
FIG. 26 is a sectional view showing a stem assembled partially within the substance-loaded barrel to form a syringe, which is in assembly with a flat-surface applicator, such as the second through the fifth applicators illustrated in FIGS. 5, 7, 13, and 15, respectively, to form a first embodiment of a syringe/applicator assembly, in accordance with certain principles of the invention.
Figure 28:
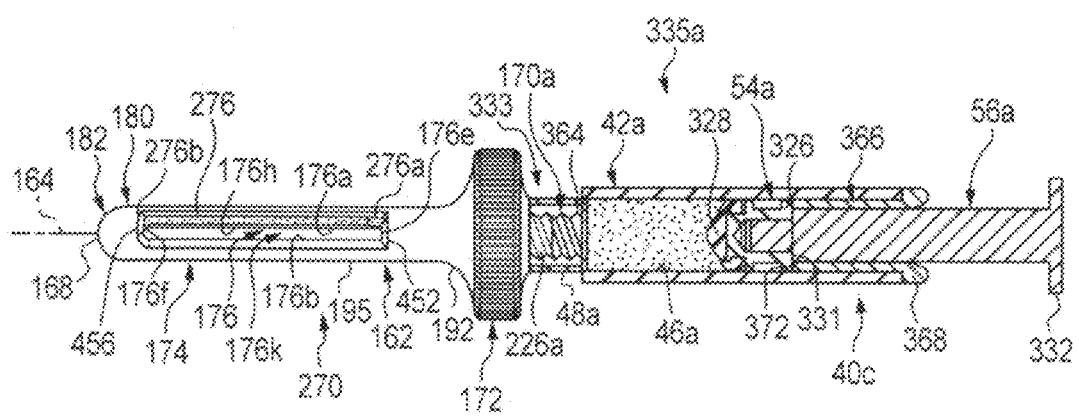
FIG. 28 is a sectional view showing a second embodiment of a syringe/applicator assembly, similar to the first embodiment assembly of FIG. 26, prepared for dispensing the barrel-contained substance, in accordance with certain principles of the invention.

Referring to FIGS. 26 and 28, the third applicator 270 is formed with the externally threaded coupler 170a (FIG. 19), as described above, which is assembled within an axially open, internally threaded sleeve 48a of a syringe 40b, described below, to form a unique flat-surface cream delivery assembly 335 (FIG. 26) and a unique flat-surface cream delivery assembly 335a (FIG. 28).

The third applicator 270, which is an element of the flat-surface cream delivery assemblies 335 and 335a, is formed with the flat surfaces 276 and 278 as described herein, and as described above, in detail, with respect to FIGS. 7 through 12, and 19. With respect to the illustration of the third applicator 270, the reference numerals appearing in FIGS. 26 and 28 are consistent with the reference numerals appearing in FIGS. 7 through 12, and 19. Therefore, the description of the third applicator 270, as it is illustrated in FIGS. 26 and 28, is the same as the above description with respect to FIGS. 7 through 12, and with respect to the above-described threaded coupler 170a illustrated in FIG. 19, all of which will suffice for a description of the third applicator in the illustration of FIGS. 26 and 28, and will not be repeated here.

It is noted that either the fourth applicator 272 (FIG. 13), with the flat surfaces 286 and 294, or the fifth applicator 274 (FIG. 15), with the flat surfaces 276d and 278d, may be assembled with the syringe 40b in place of the applicator 270, in the same manner described above with respect to the third applicator 270, to form the flat-surface cream delivery assemblies 335 and 335a, without departing from the spirit and scope of the invention.

It is further noted that any coupling structure of the syringe 40b and the applicator 270, such as, for example, the coupling structures illustrated in FIGS. 18, 20, and 21 and described above, may be used in place of the proximal coupler 170a, without departing from the spirit and scope of the invention.

Referring to FIGS. 22 through 28, described below are various unique methods of preparing the cream-loaded syringe 40b and the applicator 270 to form the assemblies 335 and 335a for use in the application of the cream 280 onto surfaces of the tissue 242 within the body opening 244 of the patient.

Figure 22:
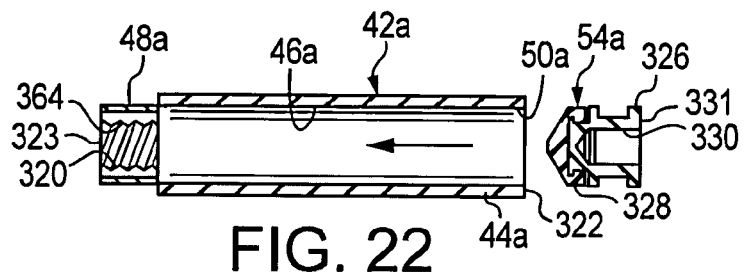
FIG. 22 is a sectional view showing a plunger head located spatially from a proximal end of a barrel of a cartridge, in accordance with certain principles of the invention.

As shown in FIGS. 22, 26 and 28, the syringe 40b is similar in structure to the syringe 40 (FIG. 1), and includes a cartridge 42a having a barrel 44a with a hollow, open-ended, barrel passage 46a extending axially therethrough. The cartridge 42a also includes, at its distal end, the axially open, internally threaded sleeve 48a. The sleeve 48a has proximal and distal openings and a threaded axial passage 320 (FIG. 22), which is in axial communication with the barrel passage 46a.

The barrel 44a is formed with a proximal opening 50a at a proximal end 322 of the cartridge 42a, and the sleeve 48a is formed with a distal opening 323 (FIG. 22), whereby the cartridge is formed with a continuously open axial passage from, and through, the proximal opening 50a to, and through, the distal opening 323. Referring further to FIGS. 22, 26, and 28, the syringe 40b includes a two-piece plunger 54a formed by a plastic proximal portion 326 and a compliant distal portion 328, which are assembled and secured together. The plastic proximal portion 326 is formed with a proximal opening 330, and with a proximal end 331.

As shown in FIGS. 26 and 28, the syringe 40b includes a stem 56a having a flange-like thumb piece or stem depressor 332 at a proximal end thereof, and an axial coupling projection 334 at a distal end thereof, which fits into, and is secured within, the proximal opening 330 (FIG. 22) of the plastic proximal portion 326 of the plunger 54a.

Figure 24:
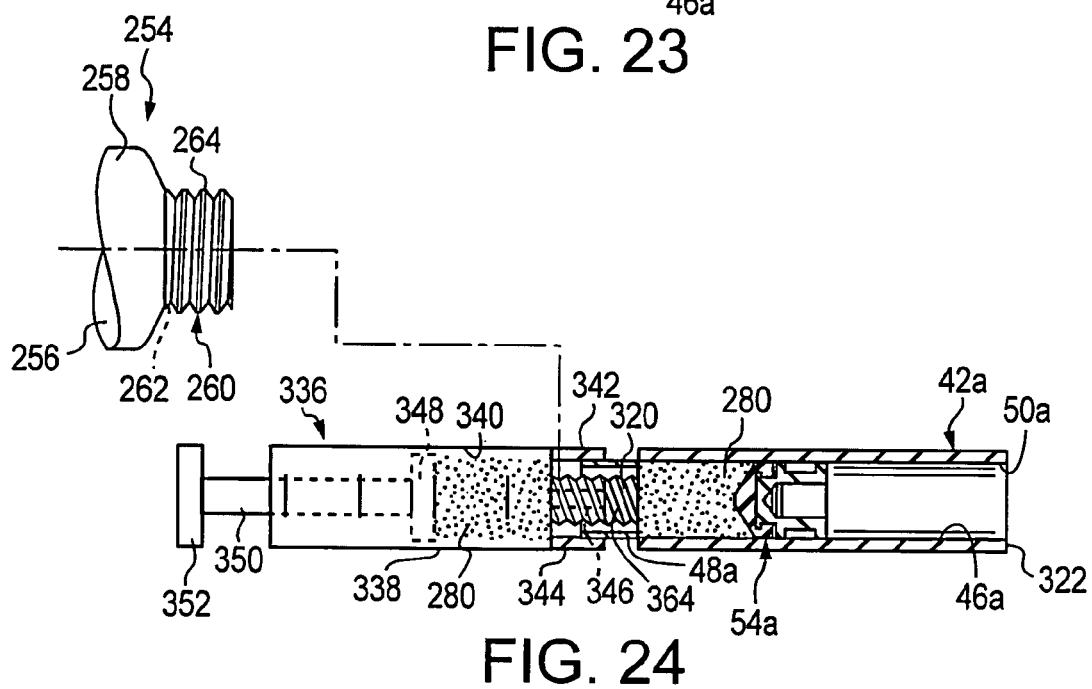
FIG. 24 is a partial sectional view showing a substance loading device, and alternately a squeeze tube, in assembly with the distal end of the barrel of FIG. 22 with the plunger head being urged away from the distal end of the barrel by the substance being deposited into the barrel, in accordance with certain principles of the invention.

As shown in FIG. 24, a syringe-like cream-supply container or dispenser 336 can be used to load the cream 280 (FIG. 12) into the syringe 40b as described below. The dispenser 336 includes a barrel 338 formed with an axial, open ended, barrel passage 340, with a sleeve 342 extending from a distal end of the barrel. An externally-threaded coupler 344 extends axially from the distal end of the barrel 338, and is located concentrically within the sleeve 342. The coupler 344 is formed with an axial coupler passage 346, which is in communication with the barrel passage 340, so that cream located within the barrel passage can flow through, and out of the distal end of, the coupler passage.

Also, the dispenser 336 includes a cream pusher head 348, which is attached to a distal end of a stem 350, and which is located within the barrel passage 340. A thumb piece or depressor 352 is attached to a proximal end of the stem 350, and is located outside of, and spaced from, a proximal end of the barrel 338. In use, a supply of the cream 280 (FIG. 12) will be contained within the barrel passage 340 of the dispenser 336, between the distal end of the barrel passage 340 and a distal side of the pusher head 348.

A squeeze-tube cream-supply container or dispenser, such as the squeeze tube 254 (FIG. 18), can be used as an alternative to the syringe-like dispenser 336 to load the cream 280 into the syringe 40b, as described below.

Figure 25:
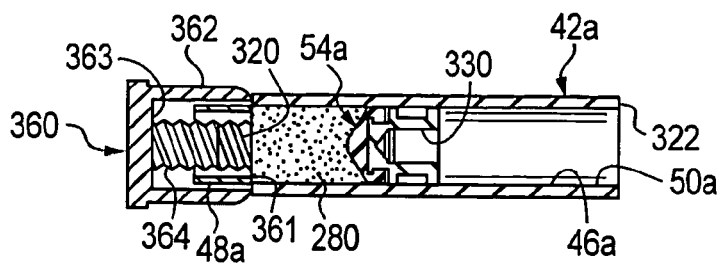
FIG. 25 is a sectional view showing a substance-loaded barrel with a cap on the distal end thereof, in accordance with certain principles of the invention.

Referring to FIG. 25, a cap 360 is formed with an axially open end 361 at one end thereof, with an axially closed end 363 at the opposite end thereof, and forms a removable protective cylindrical shell 362. A threaded projection 364 extends concentrically within the shell 362 from an inner wall of the closed end 363. After the cream 280 has been loaded into the barrel passage 46a of the cartridge 42a, as described below, the cap 360 is manipulated to insert the threaded projection 364 into the threaded axial passage 320 of the axially open sleeve 48a of the cartridge 42a, to retain the cream 280 within the barrel passage 46a between the cap and the plunger 54a.

The cap 360 may also be used to retain any cream 280 remaining within the barrel passage 46a between successive applications of the cream onto tissue 242 of the patient, in the event that the applicator 270 is removed from assembly with the syringe 40b between such successive applications of the cream.

Figure 23:
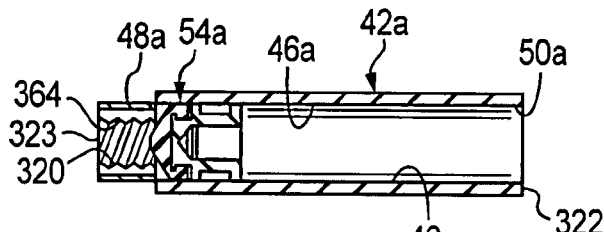
FIG. 23 is a sectional view showing the plunger head of FIG. 22 assembled within, and located a the distal end of, the barrel of FIG. 22, in accordance with certain principles of the invention.
Figure 27:
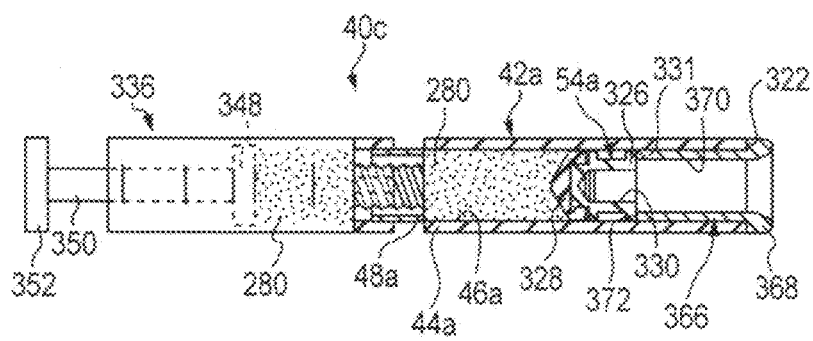
FIG. 27 is a sectional view showing the substance loading device of FIG. 26 having loaded the substance into the barrel, to urge the plunger head into engagement with a stop surface formed by the distal end of a guide located within the proximal end of the barrel, in accordance with certain principles of the invention.

Referring to FIGS. 27 and 28, prior to the loading of the cream 280 into the barrel passage 46a, and after the plunger 54a has been placed into the barrel passage, as shown in FIG. 23, a guide 366 is inserted into the proximal opening 50a of the barrel passage until a flange 368 of the guide engages the proximal end 322 of the cartridge 42a. The guide 366 is formed with an open-ended axial passage 370, through which the stem 56a is moved and guided. The guide 366 is formed with a stop surface 372 at the distal end of the guide. As shown in FIGS. 27 and 28, the stop surface 372 is located to engage the proximal end 331 of the plunger 54a, as the plunger is moved in a proximal direction by virtue of the force of the incoming cream 280 being loaded into the barrel passage 46a. This action limits the proximal travel of the plunger 54a and, thereby, the volume of the cream 280 that can be loaded into the barrel passage 46a.

Referring to FIGS. 26 and 28, it is noted that a squeeze tube, such as, for example, the squeeze tubes 254 and 254a (FIGS. 18 and 19, respectively), could be used in place of the syringe 40b to form the cream delivery assemblies 335 and 335a, without departing from the spirit and scope of the invention.

As noted above, several methods of loading an initial volume of the cream 280 into the cartridge 42a are described below, and with reference to FIGS. 22 through 28. A first of such methods includes the steps of (1) initially providing the cartridge 42a having the sleeve 48a with the barrel passage 46a and the sleeve 48a with the threaded axial passage 320, (2) inserting the plunger 54a into the barrel passage 46a from the proximal end 322 of the cartridge, (3) locating the plunger at a distal end of the barrel passage 46a, (4) depositing the initial volume of the cream 280 into the axial passage 320 through the distal opening 323 at the distal end of the cartridge; and (5) moving the plunger, within the barrel passage, toward the proximal end of the cartridge by a force of the initial volume of the substance being deposited into the distal passage.

A second method, which includes the steps of the first method described above, of loading an initial volume of a substance into the cartridge 42a, and further includes the step of placing the cap 360 over the opening at the distal end of the cartridge.

A third method, which includes the steps of the first method described above, of loading an initial volume of the cream 280 into the cartridge 42a, and further includes the steps of (1) coupling the applicator 270 to the syringe 40b at the distal opening 323 of the sleeve 48a, (2) coupling the projection 334 of the stem 56a to the plunger 54a, and (3) moving the stem, and thereby the plunger, toward the distal end of the cartridge to urge at least some of the cream 280 from the barrel passage, and into the applicator 270.

A fourth method, which includes the steps of the first method described above, of loading an initial volume of a substance into the cartridge 42a, further includes the step of providing the stop surface 372 (FIGS. 27 and 28) within the barrel passage 46a at a location at which the plunger 54a is to be located when the initial volume of the cream 280 has been deposited into the barrel passage, where, upon depositing the cream into the barrel passage, the force of the initial volume of the cream moves a proximal end of the plunger into engagement with the stop surface to preclude further depositing of the cream into the barrel passage.

Figure 29:
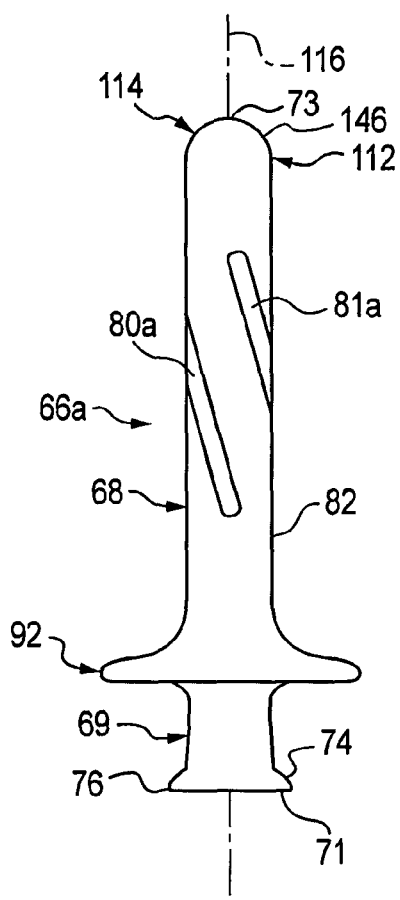
FIG. 29 is a front view showing an applicator formed with a first arrangement of slots which extend helically about a body of the applicator, in accordance with certain principles of the invention.
Figure 30:
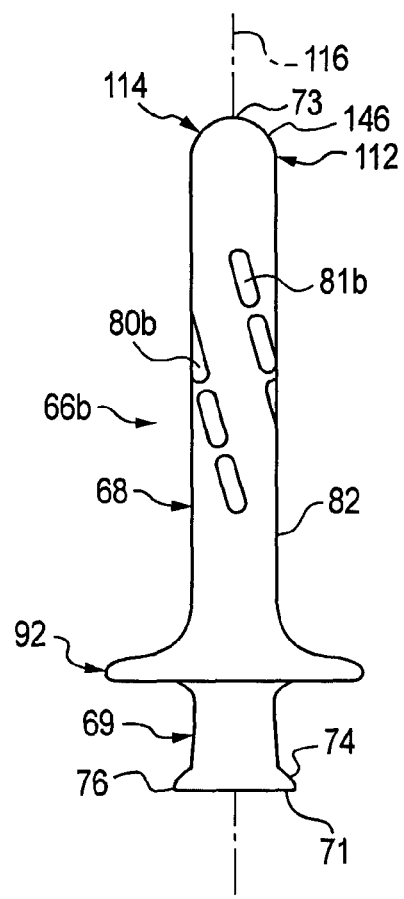
FIG. 30 is a front view showing the applicator of FIG. 29 formed with a second arrangement of slots which extend helically about a body of the applicator, in accordance with certain principles of the invention.

Referring to FIGS. 29 and 30, each of a sixth applicator 66a and a seventh applicator 66b is identical, in structure and function, to the first applicator 66, except that the slot arrangement of each of the sixth and seventh applicators is different, as described below. Other than the slot arrangement, the structural and functional features of the first applicator 66 are described above, and will not be further described here with respect to the corresponding structural and functional features of the sixth and seventh applicators.

As shown in FIG. 29, the sixth applicator 66a is formed with a first slot 80a and a second slot 81a, each of which are arranged in a helical path about the axis 116 of the body 68 of the applicator, and are spaced apart. Each of the slots 80a and 81a extend continuously from a proximal end to a distal end thereof. As the cream 280 (FIG. 12) enters the slot delivery passage 134 (FIG. 4), the cream begins to exit through proximal portions of the helical slots 80a and 81b, and is deposited onto surfaces of the tissue 242 (FIG. 12) of the patient adjacent the proximal portions of the helical slots. Eventually, the cream 280 fills the slot delivery passage 134, whereby the cream is exiting through the entire length of the helical slots 80a and 81a to deposit the cream in helical patterns onto the adjacent portion of the surfaces of the tissue 242.

As shown in FIG. 30, the seventh applicator 66b is formed with a first series of spaced slots 80b and a second series of spaced slots 81b, each series of which are arranged in a helical path about the body 68 of the applicator, with each series being spaced apart. Each of the slots 80b and 81b extend continuously from a proximal end to a distal end thereof. As the cream 280 (FIG. 12) enters the slot delivery passage 134 (FIG. 4), the cream begins to exit through the proximal-most slots 80b and 81b of each series of slots, and is deposited onto surfaces of the tissue 242 (FIG. 12) of the patient adjacent the proximal-most helical slots. Eventually, the cream 280 fills the slot delivery passage 134, whereby the cream is exiting through the entire length of each of the spaced helical slots 80a and 81a to deposit the cream in helical patterns onto the adjacent portion of the surfaces of the tissue 242.

Each of the above-described six applicators 66, 66a, 160, 270, 272, 274 is described and illustrated as being formed with two slots each; however, each of the applicators could be formed with a single slot, or more than two slots, all without departing from the spirit and scope of the invention. The above-described seventh applicator 66b is described and illustrated as being formed with the first series of helically-arranged, spaced slots 80b, and the second series of helically-arranged, spaced slots 81b. However, the seventh applicator 66b could be formed with a single series, or more than two series, of helically-arranged, spaced slots, all without departing from the spirit and scope of the invention.

As described above, each of the third applicator 270, fourth applicator 272, and fifth applicator 274 is formed with the stem 174 having the slot delivery passage 200 extending at least partially axially therethrough, along the axis 164. The slot 176 is formed transaxially through the stem 174, along a transaxis plane coincidental with the transaxis 202 which extends radially through the axis 164, to facilitate communication between the slot delivery passage 200 and the exterior of the stem adjacent the common external surface 195. The extended side wall 176b is formed in the stem to form one side of the slot 176, with the extended side wall being generally parallel to the transaxis plane.

In one embodiment, an angular side wall, in the form of either of the flat surfaces 276 or 276c of the third applicator 270, is formed in the stem 174, either of which extend away from the extended side wall 176b and the transaxis plane, to form another side of the slot, which is not parallel with the transaxis plane. In like manner, this angular side wall structural arrangement is also applicable to the slot 178.

In another embodiment, an abbreviated side wall 176h, as described above, may be alternatively formed in the stem 174 of the third applicator 270, at the another side of the slot 176, and is parallel with and spaced from the extended side wall 176b on the one side wall of the slot. The angular side wall, as described above, is joined with, and extends away from, the abbreviated side wall 176h with the abbreviated side wall and the angular side wall combining to form the another side of the slot In like manner, the angular side wall structural arrangement of the above-described one embodiment, and of the another embodiment, are also applicable to the slot 178. Also, structure similar to the above-described one embodiment and the another embodiment, is applicable to the fourth applicator 272 and the fifth applicator 274.

In general, the above-described various embodiments, as illustrated in the drawings of this application, are not to be construed as limiting the breadth of the present invention. Modifications, and other alternative constructions, will be apparent which are within the spirit and scope of the invention as defined in the appended claims.

What is claimed is:

1. An applicator for dispensing a medicinal substance therethrough, where the substance has a cream-like consistency of the type which does not flow without a force being applied thereto, which comprises:

a body formed about an axis which extends from a proximal end of the body to an exterior axial surface of a closed distal end of the body;

the body formed with a proximal section which extends from the proximal end of the body toward the closed distal end of the body, and to a distal end of the proximal section;

the proximal section of the body formed with an axial entry passage extending through the proximal section from the proximal end of the body toward the closed distal end of the body, and to a distal end of the axial entry passage;

the axial entry passage being formed with a prescribed diameter at the proximal end of the body;

the body being formed with an axial intermediate passage having a proximal end in communication with the distal end of the axial entry passage, and extending toward the closed distal end of the body, and to a distal end of the axial intermediate passage;

the axial intermediate passage being formed with a uniform passage diameter which is less than the prescribed diameter;

the body being formed about the axis thereof with a passage section, having a uniform exterior diameter, which extends from a proximal end thereof toward the closed distal end of the body, and to a distal end of the passage section;

the passage section of the body fully surrounding at least a portion of the axial intermediate passage to the distal end of the axial intermediate passage;

the body being formed about the axis thereof with a slot section, having the uniform exterior diameter, which extends from a proximal end of the slot section toward the closed distal end of the body, and to a distal end of the slot section, with the proximal end thereof being formed integrally with the distal end of the passage section;

a slot delivery passage formed axially through the slot section of the body from a proximal end thereof toward the closed distal end of the body, and to a closed distal end of the slot delivery passage, with the proximal end of the slot delivery passage being in communication with the distal end of the axial intermediate passage;

at least one axially-elongated slot formed radially through the slot section of the body in unobstructed communication with the axial slot delivery passage and an external surface of the body, and extending from the proximal end of the slot section toward the distal end of the slot section, and to a distal end of the at least one axially-elongated slot;

the slot delivery passage being formed with the uniform passage diameter interrupted only by the presence of the at least one axially-elongated slot;

the at least one elongated slot formed with an extended side wall which extends axially from a proximal end to the distal end of the at least one elongated slot;

the extended side wall located at one side of the at least one elongated slot, and extending from an inboard juncture of the extended side wall with the slot delivery passage to an outboard juncture of the extended side wall with the external surface of the body;

a flat surface formed in the body adjacent the at least one elongated slot, having a first end spaced from the extended side wall;

the flat surface extending from the first end thereof angularly away from the extended side wall to a second end of the flat surface at a juncture with the external surface of the body;

the flat surface extending axially along at least a portion of the at least one elongated slot;

the one side of the at least one elongated slot is a first side;

the extended side wall having a prescribed width dimension "W" extending between the inboard juncture to the outboard juncture thereof;

the at least one elongated slot formed with a second side spaced from the first side of the at least one elongated slot;

an abbreviated side wall spaced from the extended side wall located at the second side of the at least one elongated slot, and having a width dimension which is less than the prescribed width dimension; and the abbreviated side wall extending from an inboard juncture of the abbreviated side wall with the slot delivery passage toward the external surface of the body, and to an outboard end of the abbreviated side wall spaced inward from the external surface of the body.

2. The applicator as set forth in claim 1, which further comprises:

the body formed with a solid section, having the uniform exterior diameter, which extends from a closed proximal end of the solid section toward the closed distal end of the body, and to a closed distal end of the solid section, with the closed proximal end of the solid section being formed integrally with the distal end of the slot section.

3. The applicator as set forth in claim 2, which further comprises:

the body formed with a dome section in the form of a solid dome, which extends from a closed proximal end of the dome section to a closed distal end of the dome section, which is coincidental with the exterior axial surface of the closed distal end of the body;

the closed proximal end of the dome section being formed integrally with the closed distal end of the solid section; and the solid section and the dome section being exclusive of any opening.

4. The applicator as set forth in claim 1, which further comprises:

the flat surface extending from the first end thereof located at a juncture of the slot delivery passage and the at least one elongated slot and angularly away from the extended side wall to the second end of the flat surface at a juncture with the external surface of the body.

5. The applicator as set forth in claim 1, which further comprises:

the first end of the flat surface joined with the abbreviated side wall at the outboard end of the abbreviated side wall.

6. An applicator for dispensing a medicinal substance therethrough, which comprises:

a body formed about an axis with the body extending from a proximal end of the body to a distal end of the body;

a stem which forms an axial portion of the body;

the stem formed with a common external surface;

a slot delivery passage formed axially through at least a portion of the stem;

a slot formed through a portion of the stem from the slot delivery passage to the common external surface to facilitate the flow of the medicinal substance from within the slot delivery passage, through the slot, and to an environment adjacent the common external surface;

the slot formed with an extended side wall which extends axially from a proximal end to the distal end of the slot;

the extended side wall located at one side of the slot, and extending from an inboard juncture of the extended side wall with the slot delivery passage to an outboard juncture of the extended side wall with the common external surface of the stem;

a flat surface formed in the stem adjacent the slot, having a first end spaced from the extended side wall, the flat surface extending from the first end thereof angularly away from the extended side wall to a second end of the flat surface at a juncture with the common external surface of the stem;

the flat surface and the extended side wall extending axially along at least a portion of the slot;

the one side of the slot is a first side, which further comprises:

the extended side wall having a prescribed width dimension "W" extending between the inboard juncture to the outboard juncture thereof;

the slot formed with a second side spaced from the first side of the slot;

an abbreviated side wall spaced from the extended side wall located at the second side of the slot, and having a width dimension which is less than the prescribed width dimension; and the abbreviated side wall extending from an inboard juncture of the abbreviated side wall with the slot delivery passage toward the common external surface of the stem, and to an outboard end of the abbreviated side wall spaced inward from the common external surface of the body.

7. The applicator as set forth in claim 6, which further comprises:
a floor formed in the stem adjacent an axial end of the slot, and forming a wall of the slot; and
the floor being contiguous with the extended side wall, and extending from the extended side wall in a direction toward the first end of the flat surface.

8. The applicator as set forth in claim 7, which further comprises:
at least a portion of the floor being contiguous with, and extending toward the common external surface from, the flat surface.

9. The applicator as set forth in claim 8, which further comprises:
a transition surface formed in the stem adjacent the axial end of the slot contiguous with the floor, including the at least a portion of the floor, and having a first end located at a juncture of the transitional surface and the floor; and
the transition surface sloping axially outward from the first end thereof toward a closest axial end of the stem and to a juncture at a second end thereof with the common external surface.

10. The applicator as set forth in claim 9, which further comprises:
the floor and the transition surface forming a portion of the slot.

11. The applicator as set forth in claim 6, which further comprises:
the flat surface extending along an entire axial length of the slot.

12. The applicator as set forth in claim 6, which further comprises:
the flat surface extending along a portion of an axial length of the slot from one end of the slot toward an opposite end of the slot, and to an intermediate location along the axial length of the slot.

13. The applicator as set forth in claim 6, which further comprises:
the flat surface extending along a portion of an axial length of the slot from a first intermediate location spaced from one end of the slot toward an opposite end of the slot, and to a second intermediate location along the axial length of the slot which is spaced from the first intermediate location.

14. The applicator as set forth in claim 6, which further comprises:
the first end of the flat surface joined with the outboard end of the abbreviated side wall.

15. The applicator as set forth in claim 6, which further comprises:
the first end of the flat surface extending from an inboard juncture thereof with the slot delivery passage to an outboard juncture of the second end of the flat surface with the common external surface.

16. The applicator as set forth in claim 6, which further comprises:
a mouth of the slot located at an intersection of a wall of the slot delivery passage and the floor, with the mouth extending between a first side thereof at the intersection and a second side thereof at the intersection, spaced from the first side, with a space between the first side and the second side defining an opening of the mouth at the intersection; and the first end of the flat surface located at the second side of the mouth, with the flat surface extending to the juncture with the common external surface.

17. The applicator as set forth in claim 6, which further comprises:
the stem formed with a distal passage which extends from and through a distal end of the slot delivery passage to and through a distal end of the stem.

18. The applicator as set forth in claim 6, which further comprises:
the slot delivery passage formed with a prescribed diameter;
an axial intermediate passage formed axially through a portion of the stem and located proximally of, and in communication with, the slot delivery passage; and
the axial intermediate passage being formed with a diameter which is less than the prescribed diameter.

19. The applicator as set forth in claim 18, which further comprises:
the axial intermediate passage formed with a diameter which is the same as the prescribed diameter.

20. An applicator for dispensing a substance therethrough, which comprises:
a stem formed about an axis;
a slot delivery passage extending through the stem along at least a portion of the axis;
a common external surface formed on an exterior of the stem;
a slot formed through the stem from, and through, the slot delivery passage to, and through, the common external surface, along a transaxis extending radially through and from the axis;
an extended side wall formed in the stem, which forms one side of the slot and is generally parallel with a transaxis plane coincidental with the transaxis;
an angular side wall formed in the stem, which forms another side of the slot spaced, and extending angularly away, from the extended side wall;
an abbreviated side wall formed in the stem at the another side of the slot, which is parallel with and spaced from the extended side wall; and
the angular side wall joined with, and extending away from, the abbreviated side wall combining to form the another side of the slot.

21. An applicator for dispensing a substance therethrough, which comprises:
a stem formed with an exterior surface;
a slot delivery passage formed in the stem along a passage axis;
a slot formed through the stem from the slot delivery passage to the exterior surface of the stem along a transaxis plane extending radially from the passage axis; and
a flat surface formed in the stem contiguous with the slot and extending angularly away from the transaxis plane;
an abbreviated side wall formed in the stem at a side of the slot, which is parallel with and spaced from the transaxis plane; and
the flat surface joined with, and extending away from, the abbreviated side wall.

22. An applicator for dispensing a medicinal substance therethrough, which comprises:
a body formed about and along a body axis with the body extending from a proximal end of the body to a distal end of the body;
a stem formed along the body axis;
the stem formed with a common external surface;

a slot delivery passage formed along the body axis and through at least a portion of the stem;

a slot formed through a portion of the stem from the slot delivery passage to the common external surface and along a transaxis plane extending radially from the body axis to facilitate the flow of the medicinal substance from within the slot delivery passage, through the slot, and to an environment adjacent the common external surface;

a flat surface formed in the stem adjacent the slot, having a first end spaced from the transaxis plane;

the flat surface extending from the first end thereof angularly away from the transaxis plane to a second end of the flat surface at a juncture with the common external surface of the stem;

the flat surface extending axially along at least a portion of the slot:

the slot formed with a side spaced from the transaxis plane;

an abbreviated side wall spaced from the transaxis plane located at the side of the slot; and the abbreviated side wall extending from an inboard juncture of the abbreviated side wall with the slot delivery passage toward the common external surface of the stem, and to an outboard end of the abbreviated side wall spaced inward from the common external surface of the body.

23. The applicator as set forth in claim 22, which further comprises:

the flat surface extending along an entire axial length of the slot.

24. The applicator as set forth in claim 22, which further comprises:

the flat surface extending along a portion of an axial length of the slot from one end of the slot toward an opposite end of the slot, and to an intermediate location along the axial length of the slot.

25. The applicator as set forth in claim 22, which further comprises:

the flat surface extending along a portion of an axial length of the slot from a first intermediate location spaced from one end of the slot toward an opposite end of the slot, and to a second intermediate location along the axial length of the slot which is spaced from the first intermediate location.

26. The applicator as set forth in claim 22, which further comprises:

the first end of the flat surface joined with the outboard end of the abbreviated side wall at a juncture thereof.

27. The applicator as set forth in claim 26, which further comprises:

the flat surface extending from the juncture of the first end thereof with the outboard end of the abbreviated side wall, away from the transaxis plane, to an outboard juncture of the second end of the flat surface with the common external surface.

28. The applicator as set forth in claim 22, which further comprises:

the first end of the flat surface extending from an inboard juncture thereof with the slot delivery passage to an outboard juncture of the second end of the flat surface with the common external surface.

* * * * *